(12) United States Patent
Runco et al.

(10) Patent No.: US 8,216,241 B2
(45) Date of Patent: Jul. 10, 2012

(54) INSTRUMENTS AND METHODS FOR MANIPULATING A SPINAL FIXATION ELEMENT

(75) Inventors: Thomas J. Runco, Canton, MA (US); Michael S. Varieur, Portsmouth, RI (US); Thomas Gamache, Fall River, MA (US); Richard W. Fournier, New Bedford, MA (US)

(73) Assignee: DePuy Spine, Inc., Raynham, MA (US)

( * ) Notice: Subject to any disclaimer, the term of this patent is extended or adjusted under 35 U.S.C. 154(b) by 1277 days.

(21) Appl. No.: 11/756,318

(22) Filed: May 31, 2007

(65) Prior Publication Data
US 2007/0260261 A1 Nov. 8, 2007

Related U.S. Application Data

(63) Continuation-in-part of application No. 11/143,099, filed on Jun. 2, 2005, now abandoned.

(51) Int. Cl.
*A61B 17/70* (2006.01)
(52) U.S. Cl. .................. 606/86 A; 606/99; 606/104
(58) Field of Classification Search .............. 606/86 R, 606/96, 99, 104, 86 A, 86 B
See application file for complete search history.

(56) References Cited

U.S. PATENT DOCUMENTS

| | | |
|---|---|---|
| 410,780 A | 9/1889 | Cahn |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes et al. |
| 1,925,385 A | 9/1933 | Humes et al. |
| 2,113,246 A | 4/1938 | Frederick |
| 2,248,054 A | 7/1941 | Becker |
| 2,248,057 A | 7/1941 | Bond |
| 2,291,413 A | 7/1942 | Siebrandt |

(Continued)

FOREIGN PATENT DOCUMENTS

DE 4238339 5/1994
(Continued)

OTHER PUBLICATIONS

International Search Report (PCT/US2008/068515) dated Jan. 2, 2009.

(Continued)

*Primary Examiner* — Eduardo C Robert
*Assistant Examiner* — Jerry Cumberledge
(74) *Attorney, Agent, or Firm* — Nutter McClennen & Fish LLP

(57) ABSTRACT

An instrument for manipulating a spinal fixation element relative to a bone anchor includes a bone anchor grasping mechanism, a first adjustment mechanism, and a second adjustment mechanism. The bone anchor grasping mechanism includes a first arm having a distal end configured to engage an opening provided in the bone anchor. The first adjustment mechanism includes a second arm pivotally connected to the first arm. The second arm has a distal end configured to engage an opening provided in the bone anchor and is operable to adjust a spinal fixation element in a first direction upon pivoting relative to the first arm. The second adjustment mechanism is removably and replaceably coupled to the bone anchor grasping mechanism and is movable relative to the bone anchor grasping mechanism to adjust the spinal fixation element in a second direction, perpendicular to the first direction, relative to the bone anchor.

22 Claims, 22 Drawing Sheets

U.S. PATENT DOCUMENTS

| | | | |
|---|---|---|---|
| 2,370,407 A | 2/1945 | McCartney | |
| 2,800,820 A | 7/1957 | Retterath | |
| 3,960,147 A * | 6/1976 | Murray | 606/75 |
| 4,237,875 A | 12/1980 | Termanini | |
| 4,271,836 A | 6/1981 | Bacal et al. | |
| 4,411,259 A | 10/1983 | Drummond | |
| 4,445,513 A | 5/1984 | Ulrich et al. | |
| 4,655,223 A | 4/1987 | Kim | |
| 4,809,695 A | 3/1989 | Gwathmey et al. | |
| 4,896,661 A | 1/1990 | Bogert et al. | |
| 5,014,407 A | 5/1991 | Boughten et al. | |
| 5,020,519 A * | 6/1991 | Hayes et al. | 606/237 |
| D346,217 S | 4/1994 | Sparker et al. | |
| 5,306,248 A | 4/1994 | Barrington | |
| 5,364,397 A | 11/1994 | Hayes et al. | |
| 5,391,170 A | 2/1995 | McGuire et al. | |
| 5,429,641 A | 7/1995 | Gotfried et al. | |
| 5,484,440 A | 1/1996 | Allard | |
| 5,545,165 A | 8/1996 | Biedermann et al. | |
| 5,551,320 A | 9/1996 | Horobec et al. | |
| 5,616,143 A | 4/1997 | Schlapfer et al. | |
| 5,649,931 A | 7/1997 | Bryant et al. | |
| 5,672,175 A * | 9/1997 | Martin | 606/86 A |
| 5,683,399 A | 11/1997 | Jones | |
| 5,697,933 A | 12/1997 | Gundlapalli et al. | |
| 5,707,371 A | 1/1998 | Metz-Stavenhagen et al. | |
| 5,720,751 A * | 2/1998 | Jackson | 606/86 R |
| 5,725,532 A | 3/1998 | Shoemaker | |
| 5,746,757 A | 5/1998 | McGuire | |
| 5,782,831 A | 7/1998 | Sherman et al. | |
| 5,810,878 A | 9/1998 | Burel et al. | |
| 5,910,141 A | 6/1999 | Morrison et al. | |
| 5,941,885 A | 8/1999 | Jackson | |
| 5,951,564 A | 9/1999 | Schroder et al. | |
| 5,951,579 A | 9/1999 | Dykes | |
| 6,010,509 A | 1/2000 | Delgado et al. | |
| 6,036,692 A | 3/2000 | Burel et al. | |
| 6,099,528 A | 8/2000 | Saurat et al. | |
| 6,123,707 A | 9/2000 | Wagner | |
| 6,139,549 A | 10/2000 | Keller | |
| 6,183,472 B1 | 2/2001 | Lutz et al. | |
| 6,210,330 B1 | 4/2001 | Tepper et al. | |
| 6,251,112 B1 | 6/2001 | Jackson | |
| 6,258,090 B1 | 7/2001 | Jackson | |
| 6,371,973 B1 | 4/2002 | Tepper et al. | |
| 6,440,133 B1 * | 8/2002 | Beale et al. | 606/86 A |
| 6,440,142 B1 | 8/2002 | Ralph et al. | |
| 6,440,144 B1 | 8/2002 | Bacher | |
| 6,511,484 B2 | 1/2003 | Torode et al. | |
| 6,530,929 B1 | 3/2003 | Justis et al. | |
| 6,589,249 B2 | 7/2003 | Sater et al. | |
| 6,648,888 B1 * | 11/2003 | Shluzas | 606/86 A |
| 6,660,006 B2 | 12/2003 | Markworth et al. | |
| 6,726,692 B2 | 4/2004 | Bette et al. | |
| 6,743,231 B1 | 6/2004 | Gray et al. | |
| 6,746,449 B2 | 6/2004 | Jones et al. | |
| 6,752,832 B2 | 6/2004 | Neumann | |
| 6,755,829 B1 | 6/2004 | Bono et al. | |
| 6,790,208 B2 | 9/2004 | Oribe et al. | |
| 6,790,209 B2 | 9/2004 | Beale et al. | |
| 6,827,722 B1 | 12/2004 | Schoenefeld | |
| 7,083,621 B2 | 8/2006 | Shaolian et al. | |
| 7,156,849 B2 | 1/2007 | Dunbar et al. | |
| 7,179,254 B2 | 2/2007 | Pendekanti et al. | |
| 7,179,261 B2 | 2/2007 | Sicvol et al. | |
| 7,278,995 B2 | 10/2007 | Nichols et al. | |
| 7,320,689 B2 * | 1/2008 | Keller | 606/99 |
| 7,371,239 B2 | 5/2008 | Dec et al. | |
| 7,462,182 B2 | 12/2008 | Lim | |
| 7,485,120 B2 * | 2/2009 | Ray | 606/87 |
| 7,491,207 B2 | 2/2009 | Keyer et al. | |
| 7,527,638 B2 | 5/2009 | Anderson et al. | |
| 7,572,281 B2 | 8/2009 | Runco et al. | |
| 7,621,918 B2 | 11/2009 | Jackson | |
| 7,651,502 B2 | 1/2010 | Jackson | |
| 7,666,188 B2 | 2/2010 | Anderson et al. | |
| 7,708,763 B2 | 5/2010 | Selover et al. | |
| 7,867,237 B2 * | 1/2011 | Stad et al. | 606/90 |
| 7,887,541 B2 | 2/2011 | Runco et al. | |
| 7,988,698 B2 | 8/2011 | Rosenberg et al. | |
| 2001/0029376 A1 | 10/2001 | Sater et al. | |
| 2002/0095153 A1 | 7/2002 | Jones et al. | |
| 2003/0009168 A1 | 1/2003 | Beale et al. | |
| 2003/0028195 A1 | 2/2003 | Bette | |
| 2003/0083747 A1 * | 5/2003 | Winterbottom et al. | 623/17.11 |
| 2003/0125750 A1 | 7/2003 | Zwimmann et al. | |
| 2003/0149438 A1 | 8/2003 | Nichols et al. | |
| 2003/0191370 A1 | 10/2003 | Phillips | |
| 2003/0199872 A1 | 10/2003 | Markworth et al. | |
| 2003/0225408 A1 * | 12/2003 | Nichols et al. | 606/61 |
| 2004/0049191 A1 | 3/2004 | Markworth et al. | |
| 2004/0147936 A1 | 7/2004 | Rosenberg et al. | |
| 2004/0147937 A1 | 7/2004 | Dunbar et al. | |
| 2004/0172057 A1 | 9/2004 | Guillebon et al. | |
| 2004/0176779 A1 | 9/2004 | Casutt et al. | |
| 2004/0220567 A1 | 11/2004 | Eisermann et al. | |
| 2004/0254576 A1 | 12/2004 | Dunbar et al. | |
| 2004/0267275 A1 | 12/2004 | Cournoyer et al. | |
| 2005/0015094 A1 * | 1/2005 | Keller | 606/99 |
| 2005/0015095 A1 | 1/2005 | Keller | |
| 2005/0033299 A1 | 2/2005 | Shluzas | |
| 2005/0055031 A1 | 3/2005 | Lim | |
| 2005/0059969 A1 | 3/2005 | McKinley | |
| 2005/0079909 A1 | 4/2005 | Singhaseni | |
| 2005/0090824 A1 | 4/2005 | Shluzas et al. | |
| 2005/0131408 A1 | 6/2005 | Sicvol et al. | |
| 2005/0131420 A1 | 6/2005 | Techiera et al. | |
| 2005/0131421 A1 | 6/2005 | Anderson et al. | |
| 2005/0131422 A1 | 6/2005 | Anderson et al. | |
| 2005/0143749 A1 | 6/2005 | Zalenski et al. | |
| 2005/0149036 A1 | 7/2005 | Varieur et al. | |
| 2005/0149048 A1 | 7/2005 | Leport et al. | |
| 2005/0149053 A1 | 7/2005 | Varieur et al. | |
| 2005/0192570 A1 | 9/2005 | Jackson | |
| 2005/0192579 A1 | 9/2005 | Jackson | |
| 2005/0228392 A1 | 10/2005 | Keyer et al. | |
| 2005/0261702 A1 | 11/2005 | Oribe et al. | |
| 2006/0009775 A1 | 1/2006 | Dec et al. | |
| 2006/0025768 A1 | 2/2006 | Iott et al. | |
| 2006/0036254 A1 | 2/2006 | Lim | |
| 2006/0036260 A1 | 2/2006 | Runco et al. | |
| 2006/0069391 A1 | 3/2006 | Jackson | |
| 2006/0074418 A1 | 4/2006 | Jackson | |
| 2006/0079909 A1 | 4/2006 | Runco et al. | |
| 2006/0089651 A1 * | 4/2006 | Trudeau et al. | 606/86 |
| 2006/0095035 A1 | 5/2006 | Jones et al. | |
| 2006/0111712 A1 | 5/2006 | Jackson | |
| 2006/0111713 A1 | 5/2006 | Jackson | |
| 2006/0111730 A1 | 5/2006 | Hay | |
| 2006/0166534 A1 | 7/2006 | Brumfield et al. | |
| 2006/0166535 A1 | 7/2006 | Brumfield et al. | |
| 2006/0293692 A1 | 12/2006 | Whipple et al. | |
| 2007/0093849 A1 | 4/2007 | Jones et al. | |
| 2007/0129731 A1 | 6/2007 | Sicvol et al. | |
| 2007/0161998 A1 | 7/2007 | Whipple | |
| 2007/0167954 A1 | 7/2007 | Sicvol et al. | |
| 2007/0173831 A1 | 7/2007 | Abdou | |
| 2007/0185375 A1 | 8/2007 | Stad et al. | |
| 2007/0213722 A1 | 9/2007 | Jones et al. | |
| 2007/0233097 A1 | 10/2007 | Anderson et al. | |
| 2007/0260261 A1 | 11/2007 | Runco et al. | |
| 2007/0270880 A1 | 11/2007 | Lindemann et al. | |
| 2008/0077134 A1 | 3/2008 | Dziedzic et al. | |
| 2008/0077135 A1 | 3/2008 | Stad et al. | |
| 2008/0243190 A1 | 10/2008 | Dziedzic et al. | |
| 2008/0255574 A1 | 10/2008 | Dye | |
| 2009/0030419 A1 | 1/2009 | Runco et al. | |
| 2009/0030420 A1 | 1/2009 | Runco et al. | |
| 2009/0054902 A1 | 2/2009 | Mickiewicz et al. | |
| 2009/0082811 A1 | 3/2009 | Stad et al. | |
| 2009/0088764 A1 | 4/2009 | Stad et al. | |
| 2009/0138056 A1 | 5/2009 | Anderson et al. | |
| 2009/0143828 A1 | 6/2009 | Stad et al. | |
| 2010/0137915 A1 | 6/2010 | Anderson et al. | |
| 2011/0034961 A1 | 2/2011 | Runco et al. | |
| 2011/0144695 A1 | 6/2011 | Rosenberg et al. | |

FOREIGN PATENT DOCUMENTS

| | | |
|---|---|---|
| DE | 29806563 U1 | 6/1998 |
| EP | 948939 A2 | 10/1999 |
| EP | 1574175 | 9/2005 |
| EP | 1648320 | 4/2006 |
| EP | 1796564 | 6/2007 |
| FR | 2677242 | 12/1992 |
| FR | 2680314 A1 | 2/1993 |
| FR | 2729291 | 1/1995 |
| FR | 2729291 A1 | 7/1996 |
| WO | 9621396 A1 | 7/1996 |
| WO | 2005006948 A2 | 1/2005 |
| WO | 2006020443 A1 | 2/2006 |

OTHER PUBLICATIONS

U.S. Patent No. 6,790,209 Reissue Application Declaration and related Transmittal Letter and Information Disclosure Statement citing schematic drawings from Sofamor, "Introducteur—Contreur De Tige", Jan. 1, 1994.

U.S. Appl. No. 11/539,496, Dziedzic et al.

International Search Report and Written Opinion mailed Nov. 6, 2008 for Application No. PCT/US2008/072851.

* cited by examiner

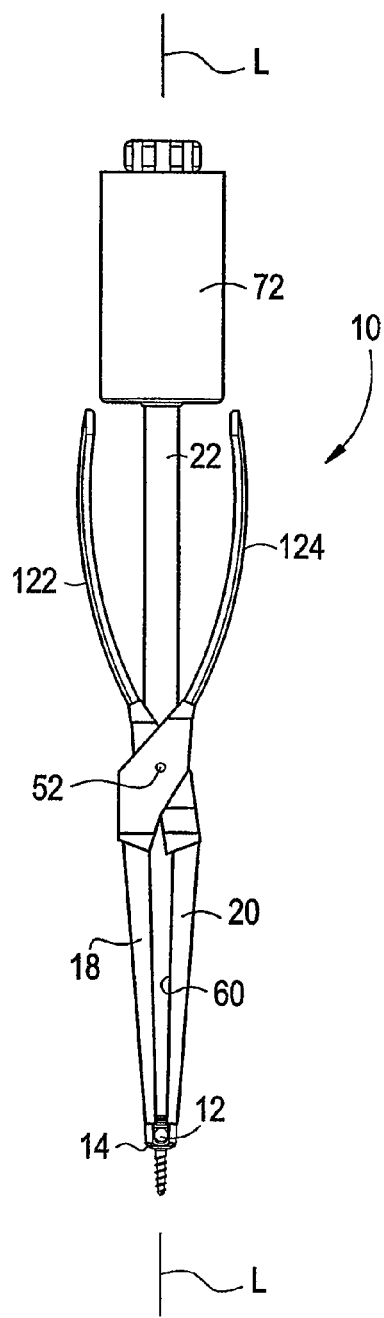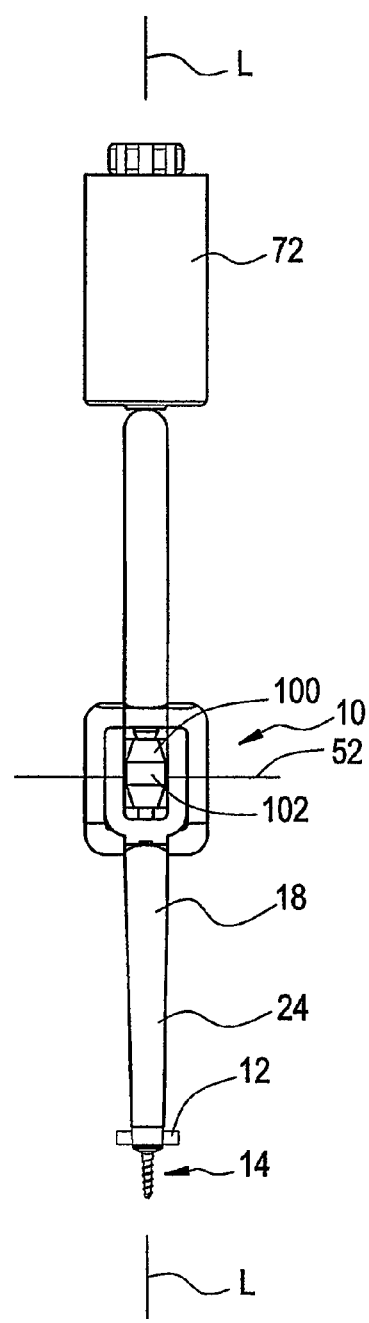

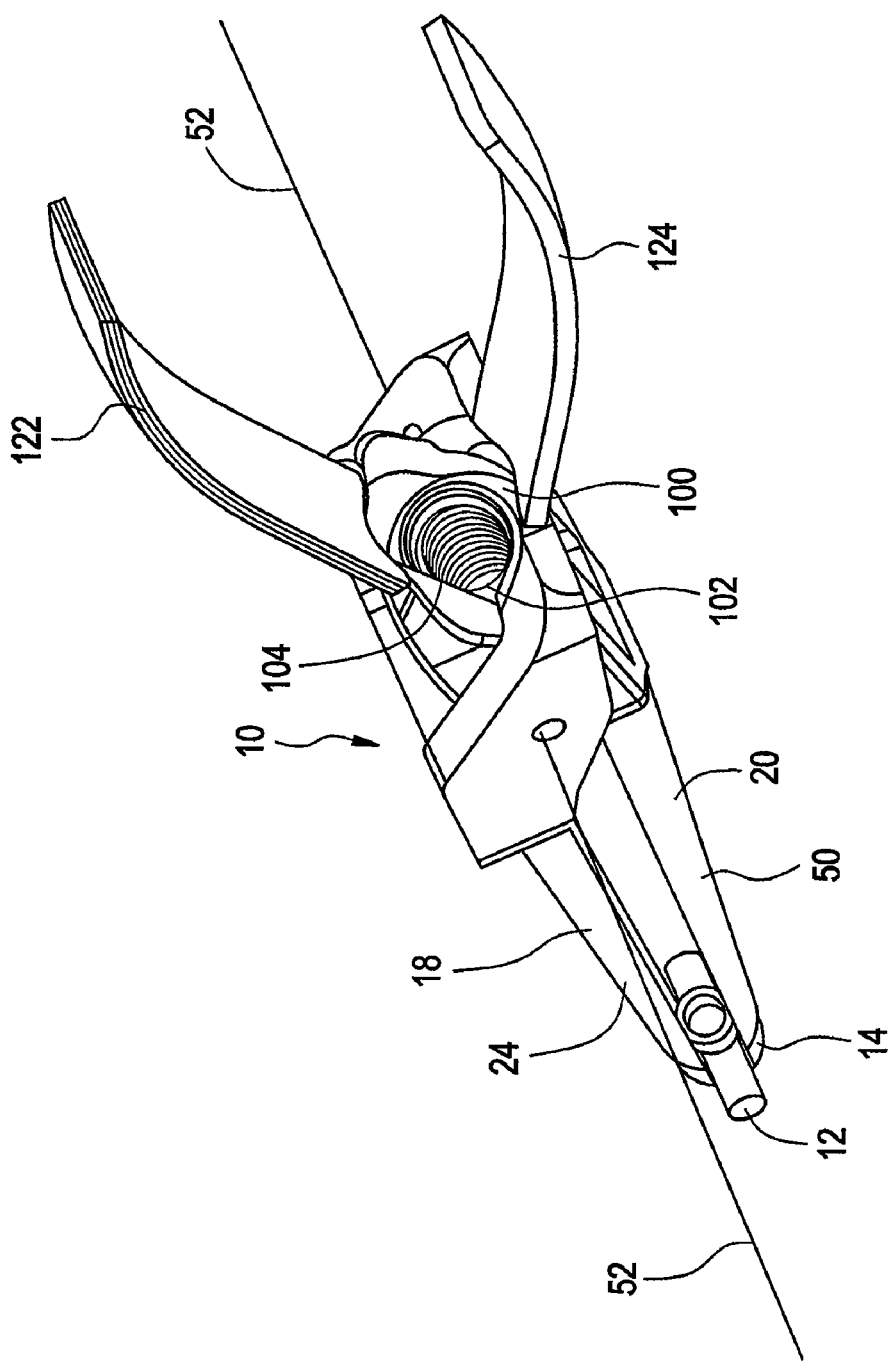

FIG. 7
FIG. 8
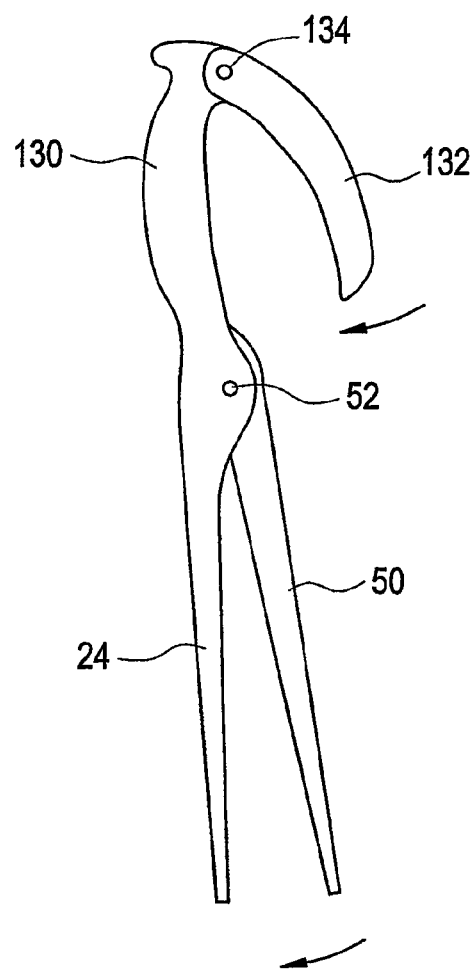
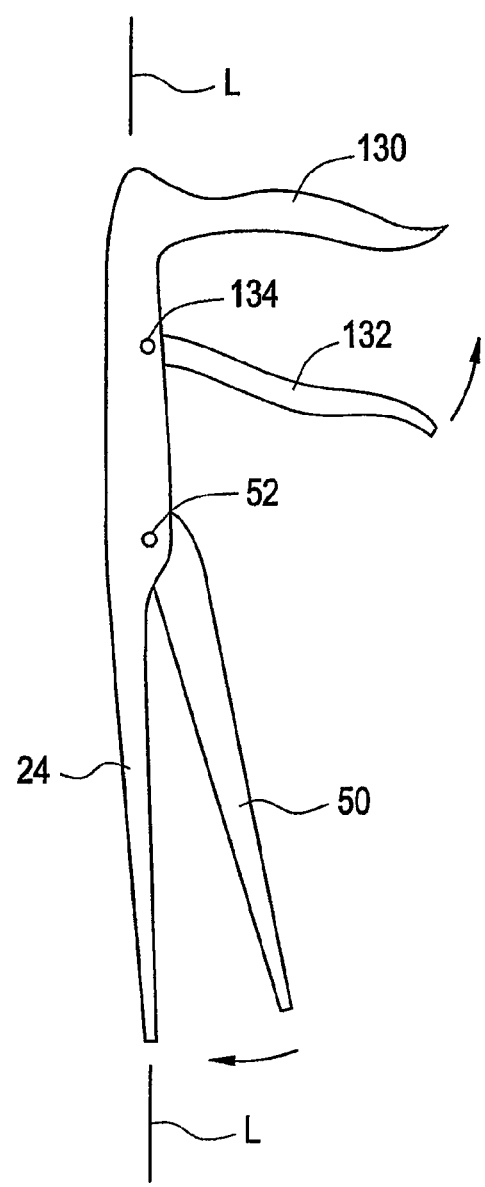

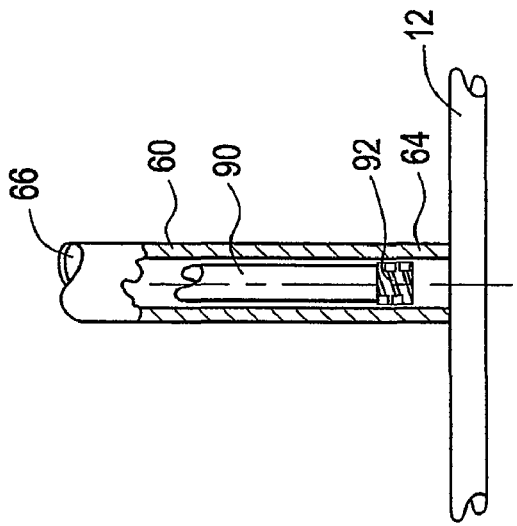
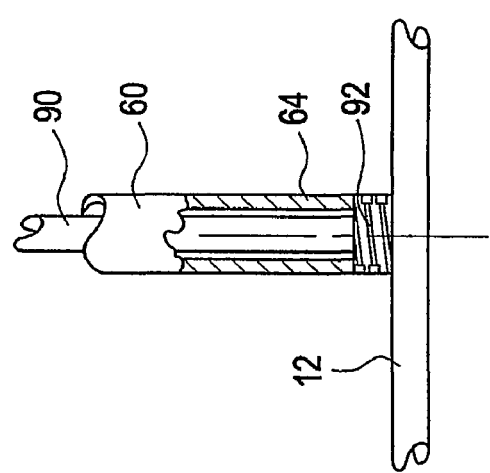
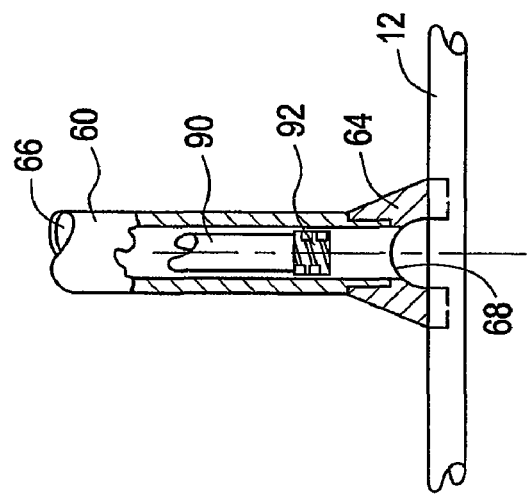

INSTRUMENTS AND METHODS FOR MANIPULATING A SPINAL FIXATION ELEMENT

CROSS REFERENCE TO RELATED APPLICATION

The present application is a continuation-in-part of co-pending U.S. patent application Ser. No. 11/143,099, filed Jun. 2, 2005.

BACKGROUND

Spinal fixation systems may be used in orthopedic surgery to align and/or fix a desired relationship between adjacent vertebrae. Such systems typically include a spinal fixation element, such as a relatively rigid fixation rod or plate or a relatively flexible tether or cable, that is coupled to adjacent vertebrae by attaching the element to various anchoring devices, such as hooks, bolts, wires, or screws. The spinal fixation element can have a predetermined contour that has been designed according to the properties of the target implantation site, and once installed, the spinal fixation element holds the vertebrae in a desired spatial relationship, either until desired healing or spinal fusion has taken place, or for some longer period of time.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal fixation element receiving element, which, in spinal rod applications, is usually in the form of a U-shaped slot formed in the head for receiving the rod. A set-screw, plug, cap or similar type of closure mechanism, is used to lock the rod into the rod-receiving portion of the pedicle screw. In use, the shank portion of each screw is then threaded into a vertebra, and once properly positioned, a fixation rod is seated through the rod-receiving portion of each screw and the rod is locked in place by tightening a cap or similar type of closure mechanism to securely interconnect each screw and the fixation rod. Other anchoring devices also include hooks and other types of bone screws.

While current spinal fixation systems have proven effective, difficulties have been encountered in mounting rods, or other spinal fixation elements, into the rod-receiving portion of various fixation devices. In particular, it can be difficult to align and seat the rod into the rod receiving portion of adjacent fixation devices due to the positioning and rigidity of the vertebra into which the fixation device is mounted. Thus, the use of a spinal rod approximator, also referred to as a spinal rod reducer, is often required in order to grasp the head of the fixation device, and reduce the rod into the rod-receiving portion of the fixation device.

While several rod approximators are known in the art, some tend to be difficult and very time-consuming to use. Accordingly, there is a need for an improved rod approximator and methods for seating a spinal rod in a rod-receiving portion of one or more spinal implants.

SUMMARY

Disclosed herein are instruments and methods for manipulating a spinal fixation element, such as a spinal rod, relative to a bone anchor, such as a polyaxial or monoaxial bone screw. The instruments and methods disclosed herein are particularly suited for lateral and vertical alignment of a spinal fixation element relative to a bone anchor.

In accordance with one exemplary embodiment, an instrument for manipulating a spinal fixation element relative to a bone anchor may comprise a bone anchor grasping mechanism, a first adjustment mechanism and a second adjustment mechanism. In the exemplary embodiment, the bone anchor grasping mechanism may include a first arm having a distal end configured to engage an opening provided in the bone anchor. The first adjustment mechanism may include a second arm pivotally connected to the first arm. The second arm may have a distal end configured to engage an opening provided in the bone anchor and may be operable to adjust a spinal fixation element in a first direction upon pivoting relative to the first arm. The second adjustment mechanism may be coupled to at least one of the bone anchor grasping mechanism and the first adjustment mechanism and may be movable relative to the bone anchor grasping mechanism to adjust the spinal fixation element in a second direction, perpendicular to the first direction, relative to the bone anchor.

In accordance with another exemplary embodiment, an instrument for manipulating a spinal fixation element relative to a bone anchor may comprise a first arm, a second arm pivotally connected to the first arm, and adjustment mechanism coupled to the first arm and the second arm. In the exemplary embodiment, the first arm may have a distal end having an arcuate projection for engaging a first arcuate groove provided in the bone anchor. The second arm may have a distal end having an arcuate projection for engaging a second arcuate groove provided in the bone anchor. The first arm and second arm may be pivotable about a pivot axis that intersects the first arm and second arm and the second arm may be operable to adjust a spinal fixation element in a first direction upon pivoting relative to the first arm. The adjustment mechanism may be movable relative to the bone anchor grasping mechanism to adjust the spinal fixation element in a second direction, perpendicular to the first direction, relative to the bone anchor.

In accordance with another exemplary embodiment, an instrument for manipulating a spinal fixation element relative to a bone anchor may comprise a first arm, a second arm pivotally connected to the first arm, an adjustment mechanism coupled to first arm and the second arm, and a coupling mechanism connected to the first arm and the second arm. The first arm may have a distal end having a projection for engaging a first opening provided in the bone anchor and the second arm may have a distal end having a projection for engaging a second opening provided in the bone anchor. The first arm and second arm may be pivotable about a pivot axis that intersects the first arm and second arm and the second arm may be operable to adjust a spinal fixation element in a first direction upon pivoting relative to the first arm. The adjustment mechanism may be movable relative to the bone anchor grasping mechanism to adjust the spinal fixation element in a second direction, perpendicular to the first direction, relative to the bone anchor. The coupling mechanism may be positioned between the first arm and the second arm such that the pivot axis intersects the coupling mechanism. The coupling mechanism may be configured to receive the adjustment mechanism and permit motion of the adjustment mechanism relative to the first arm and the second arm.

In accordance with another exemplary embodiment, an instrument for manipulating a spinal fixation element relative to a bone anchor may comprise a bone anchor grasping mechanism, a first adjustment mechanism and a second adjustment mechanism. In the exemplary embodiment, the bone anchor grasping mechanism may include a first arm having a proximal end with a handle portion, a distal end configured to engage a first receiving portion provided on the bone anchor, and an intermediate portion disposed between the proximal and distal ends. The intermediate portion may have a housing with a threaded bore formed therein. The first adjustment mechanism may include a second arm pivotally connected to the housing of the first arm. The second arm may have a proximal end with a handle portion and a distal end configured to engage a second receiving portion provided on the bone anchor. Furthermore, the second arm may be operable to adjust a spinal fixation element in a first direction upon pivoting relative to the first arm. The second adjustment mechanism may have a threaded portion configured to be removably and replaceably coupled to the threaded bore of the housing of the first arm and may be movable relative to the bone anchor grasping mechanism to adjust the spinal fixation element in a second direction, perpendicular to the first direction, relative to the bone anchor.

In accordance with another exemplary embodiment, an instrument for manipulating a spinal fixation element relative to a bone anchor may comprise a first arm, a second arm pivotally connected to the first arm, a housing coupled to at least one of the first arm and the second arm, and an adjustment mechanism, which optionally can be removably and replaceably coupled to the housing. In the exemplary embodiment, the first arm may have a proximal end with a handle portion and a distal end configured to engage a first receiving portion provided on the bone anchor. The second arm may have a proximal end with a handle portion and a distal end configured to engage a second receiving portion provided on the bone anchor. The first arm and the second arm may be pivotable about a pivot axis that intersects the first arm and the second arm and at least one of the first arm and the second arm may be operable to adjust a spinal fixation element in a first direction upon pivoting relative to the other arm. The housing may have a threaded bore formed therein. The adjustment mechanism may have a threaded portion configured to selectively mate with the threaded bore of the housing and the adjustment mechanism may be movable relative to at least one of the first arm and the second arm to adjust the spinal fixation element in a second direction that is generally perpendicular to the first direction, relative to the bone anchor.

BRIEF DESCRIPTION OF THE FIGURES

These and other features and advantages of the instruments and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

FIG. 2 is a front view of the instrument of FIG. 1;

FIG. 3 is a side view of the instrument of FIG. 1;

FIG. 4 is a top perspective view of the instrument of FIG. 1;

FIG. 7 is a side view of another exemplary embodiment of an instrument for manipulating a spinal fixation element relative to a bone anchor;

FIG. 8 is a side view of another exemplary embodiment of an instrument for manipulating a spinal fixation element relative to a bone anchor, illustrating the lateral activation mechanism of the instrument;

FIGS. 11A-11C are side views of alternative exemplary embodiments of the distal end of the adjustment mechanism, illustrating alternative mechanisms for interacting with the spinal fixation element;

DETAIL DESCRIPTION OF EXEMPLARY EMBODIMENTS

Figure 1:
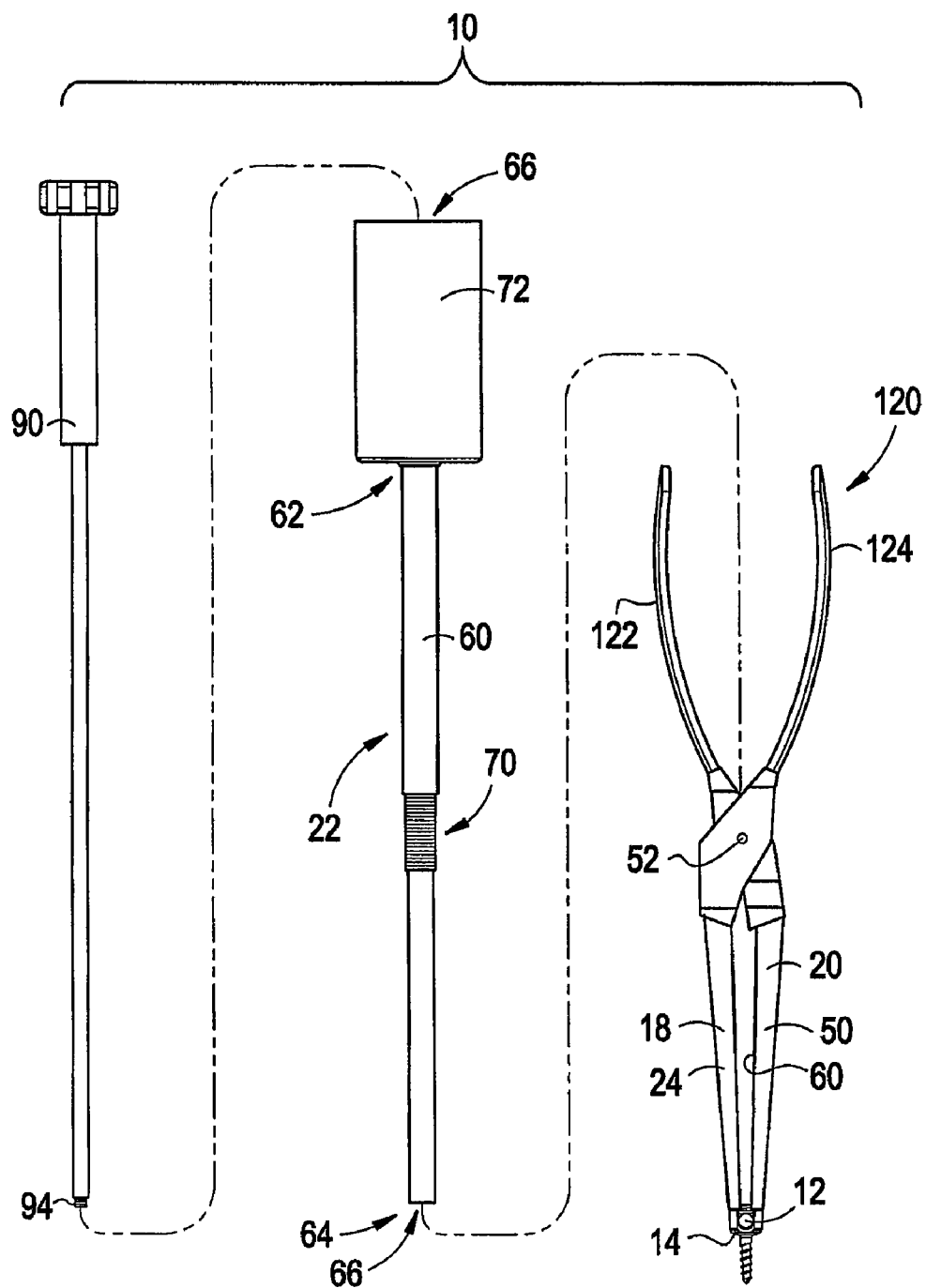
FIG. 1 is an assembly view of an exemplary embodiment of an instrument for manipulating a spinal fixation element relative to a bone anchor.
Figure 5:
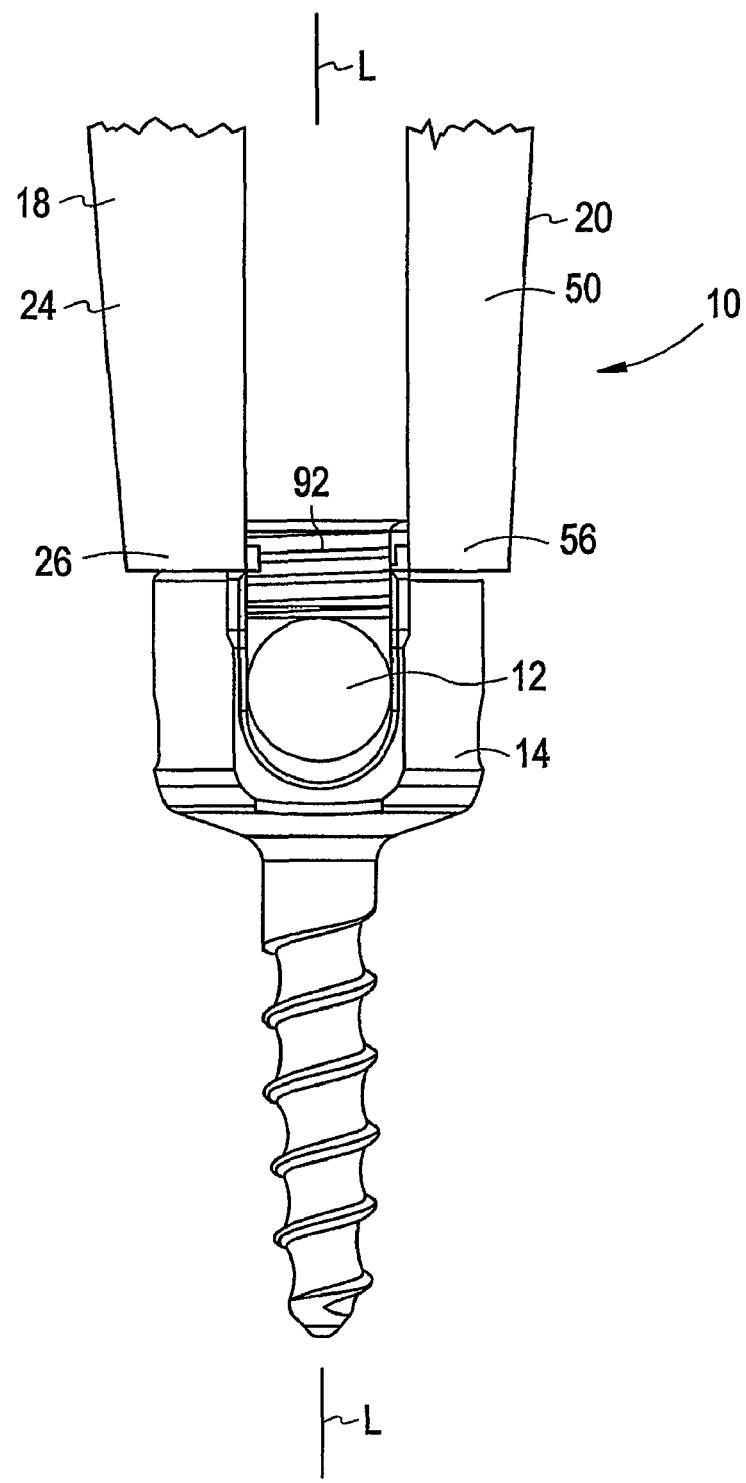
FIG. 5 is a side view of the distal end of the instrument of FIG. 1.

Certain exemplary embodiments will now be described to provide an overall understanding of the principles of the structure, function, manufacture, and use of the instruments and methods disclosed herein. One or more examples of these embodiments are illustrated in the accompanying drawings.

Those of ordinary skill in the art will understand that the instruments and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element"means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-6 and 13 illustrate an exemplary embodiment of an instrument 10 for manipulating a spinal fixation element 12, such as, for example, a spinal rod, a plate, a tether or cable or combinations thereof, relative to a bone anchor 14, such as, for example, a bone screw or hook. The exemplary instrument 10 is particularly suited adjust a spinal fixation element in two directions relative to a bone anchor. For example, the exemplary instrument 10 is suited for both lateral adjustment of the spinal fixation element 12 and vertical adjustment of the spinal fixation element 12 relative to the bone anchor 14. The exemplary instrument 10 includes a bone anchor grasping mechanism 18 configured to engage an opening in the bone anchor 14, a first adjustment mechanism 20 operable to adjust the spinal fixation element 12 in a first direction relative to the bone anchor 14 and a second adjustment mechanism 22 operable to adjust the spinal fixation element 10 in a second direction, at an angle to the first direction, e.g., perpendicular to the first direction, relative to the bone anchor 14.

As illustrated and in the description of the exemplary instrument 10 that follows the spinal fixation element is a spinal rod 12 and the bone anchor is a monoaxial bone screw 14. One skilled in the art will appreciate that the spinal fixation element and the bone anchor are not limited to the illustrated exemplary embodiments. The instrument may be used with any type of spinal fixation element and any type of bone anchor.

The bone anchor grasping mechanism 18 of the exemplary instrument 10 may include a first arm 24 having a distal end 26 configured to releasably engage a bone anchor. For example, the first arm 24 may be engaged to a bone anchor in a manner that allows the first arm 24, and thus the instrument 10, to be connected to the bone anchor 14 during use, e.g., during adjustment of the spinal fixation element 12 relative to the bone anchor 14, and allows the first arm 24, and thus, the instrument 10, to be disconnected from the bone anchor 14 at the conclusion of the procedure. Preferably, the first arm 24 can be disconnected remotely. For example, the exemplary embodiment, the first arm 24 can be disconnected from the bone anchor by manipulation of the proximal end of the first arm 24.

Figure 6:
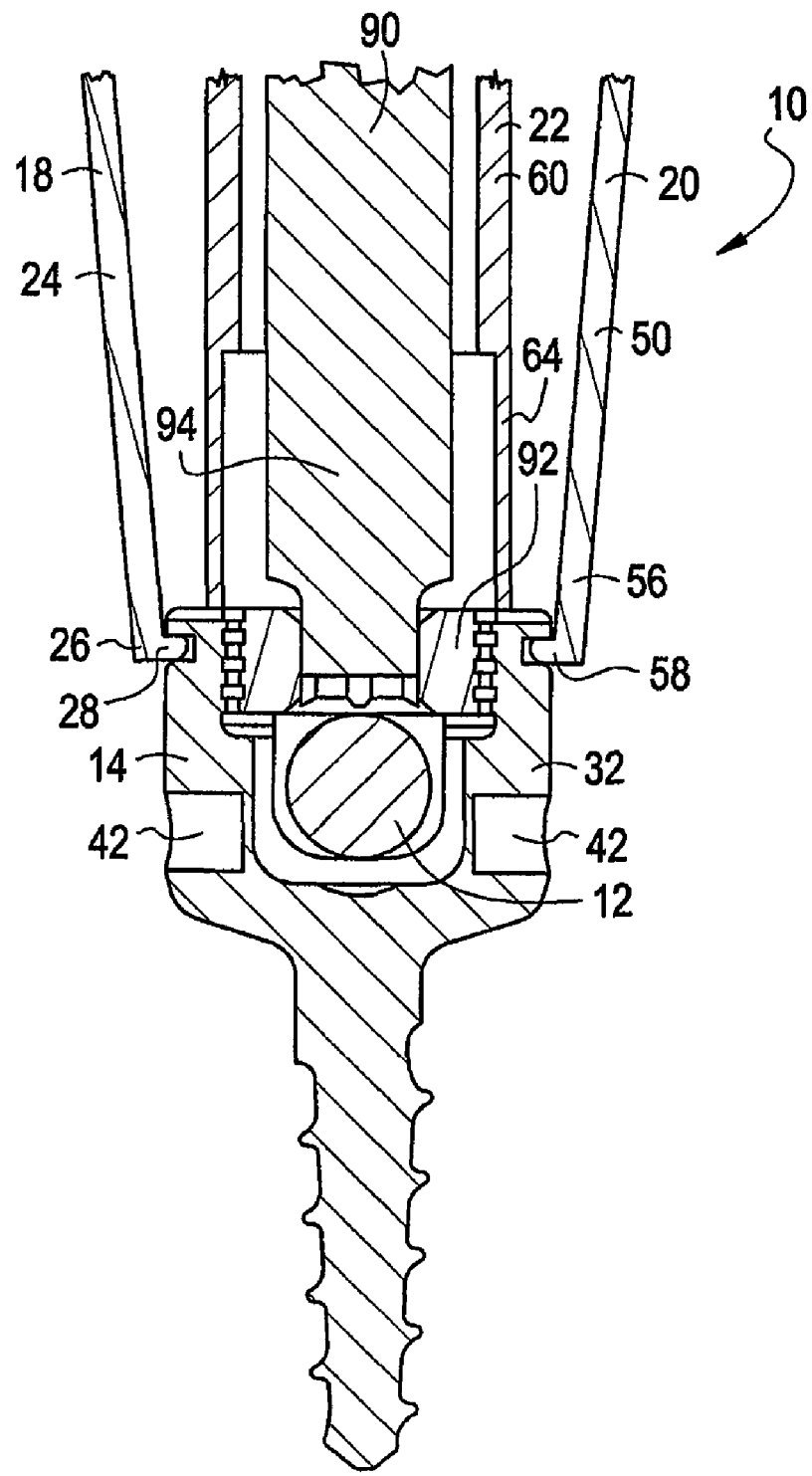
FIG. 6 is a side view in cross section of the distal end of the instrument of FIG. 1.
Figure 12B:
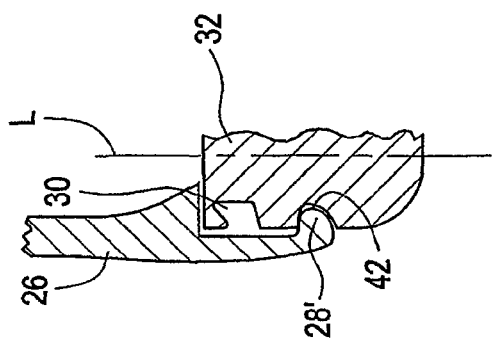
FIGS. 12A-12D are side views of alternative exemplary embodiments of the distal end of the first arm of the instrument, illustrating alternative bone anchor engagement mechanisms.
Figure 12A:
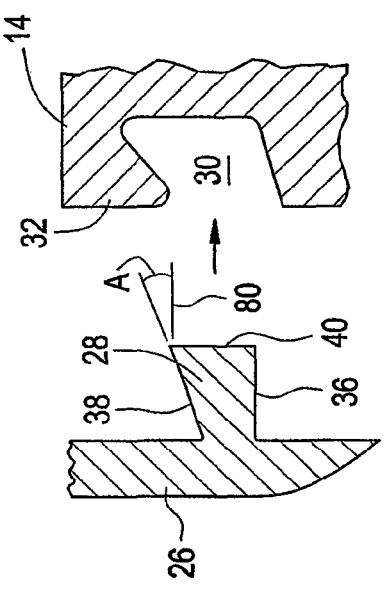

Referring to FIGS. 6, 12A and 12B, the distal end 26 of the first arm 24 may be configured to engage an opening provided in the bone anchor 14. For example, the distal end 26 of the first arm 24 may include one or more radially inward facing projection 28 that is sized and shaped to seat within an opening provided in a portion of the bone anchor. The size, shape and number of projections can be varied depending on, for example, the opening(s) provided on the bone anchor and type of connection desired. In the illustrated exemplary embodiment, for example, the projection 28 is generally arcuate in shape and has a cross section and a curvature that is complementary to an arcuate groove 30 provided in the spinal fixation element receiving member 32 of the exemplary bone anchor 14. Exemplary bone anchors having such features are described in U.S. patent application Ser. No. 10/738,286, filed Dec. 16, 2003, incorporated herein by reference. In particular, the projection 28 has a distal surface 36, a proximal surface 38, and a generally radially facing connecting surface 40 that spans between the distal surface 36 and the proximal surface 38, as shown in FIG. 12B. In the illustrated embodiment, the distal surface 36 is generally oriented perpendicular to the longitudinal axis L of the instrument 10 and the connecting surface 40 is generally oriented parallel to the longitudinal axis L of the instrument 10 and perpendicular to the distal surface 36. One or both of the proximal surface 38 and the distal surface 36 may be oriented at an angle other than perpendicular to the longitudinal axis L of the instrument 10. For example, the proximal surface 38 may be oriented at an angle A to an orthogonal line 80, which is oriented perpendicular to the longitudinal axis L of the instrument 10. In the exemplary embodiment, the angle A may be approximately 5° to approximately 30° and is preferably approximately 20°. The distal surface 36 and the proximal surface 38 may be oriented at the same angle or, as in the exemplary embodiment, may be oriented at different angles.

Figure 12C:
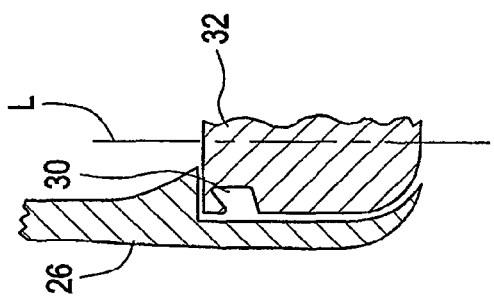
Figure 12D:
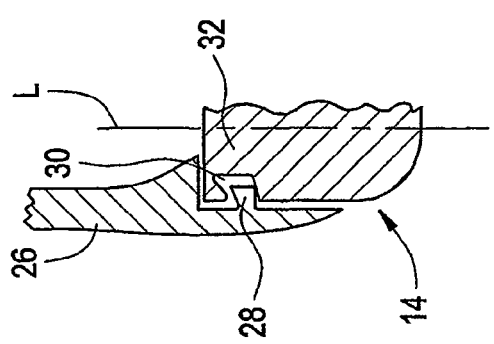

In alternative embodiments, the distal end 26 of the first arm 24 may include additional and/or alternatively positioned and/or shaped projections. For example, the distal end 26 of the first arm 24 may include a projection 28' configured to engage a swaged opening positioned between the proximal and distal ends of the spinal fixation element receiving member 32 of the exemplary bone anchor 14, as illustrated in FIG. 12C. The projection 28' may be generally cylindrical in shape, may be generally hemispherical in shape, or may have other suitable shapes. In alternative embodiments, the distal end 26 may include two projections, e.g., the arcuate projection 28 illustrated in FIGS. 12A and 12B and the projection 28' illustrated in FIG. 12C. In alternative embodiments, the distal end 26 of the first arm 24 may not include a projection. For example, the distal end 26 may be sized and shaped to engage the distal end of the of the spinal fixation element receiving member 32 of the exemplary bone anchor 14, as illustrated in FIG. 12D.

Continuing to refer to FIGS. 1-6 and 13, in the exemplary instrument, the first adjustment mechanism 20 may include a second arm 50 that is pivotally connected to the first arm 24 and is operable to adjust the spinal fixation element 12 in a first direction upon pivoting of the second arm 50 relative to the first arm 24. For example, the first arm 24 may be directly pivotally connected to the second arm 50 such that the first arm 24 and the second arm 50 pivot about a pivot axis 52 that intersects the first arm 24 and the second arm 50. In alternative embodiments, the first arm 24 may be indirectly pivotally connected to the second arm 50, for example, the first arm 24 may be off set from the second arm 50 such that the first arm 24 and the second arm 50 pivot about a pivot axis that does not intersect both the first arm 24 and the second arm 50.

The second arm 50 may have a distal end 56 configured to releasably engage the bone anchor 14. The distal end 56 of the second arm 50 may be configured in a manner analogous to the distal end 26 of the first arm 24. For example, the distal end 56 of the second arm 50 may include a projection 58 sized and shape to engage an opening in the bone anchor 14.

The inner surface 60 of the second arm 50 of the exemplary instrument 10 may be configured to facilitate contact with and adjustment of the spinal fixation element 12 relative to the bone anchor. For example, the inner surface 60 of the second arm 50 may be coated with a material having a relatively low coefficient of friction to facilitate movement of the spinal fixation element 12 along the inner surface 60 of the second arm 50 during adjustment of the spinal fixation element in the first direction.

Continuing to refer to FIGS. 1-6 and 13, the second adjustment mechanism 22 may be coupled to the first arm 24 and/or the second arm 50 and may be movable relative to the first arm 24 and/or the second arm 50 to adjust the spinal fixation element 12 relative to the bone anchor 14 in a second direction that is different to, e.g., at an angle to, the first direction. In the illustrated embodiment, the second adjustment mechanism 22 comprises an elongated tubular body 60 having a proximal end 62 and a distal end 64 and a lumen 66 extending between the proximal end 62 and the distal end 64. The lumen 66 may be sized and shaped to permit a closure mechanism delivery instrument 90 to be positioned therethrough. The closure mechanism delivery instrument 90 is provided for the delivery of a closure mechanism 92, for example, a set screw or the like, to the bone anchor 14 to secure the spinal fixation element 12 relative to the bone anchor 12 after alignment of the spinal fixation element 12. In the illustrated embodiment, the closure mechanism delivery instrument 90 is a screwdriver having a distal end 94 with external threads for engaging the closure mechanism 92.

Figure 13:
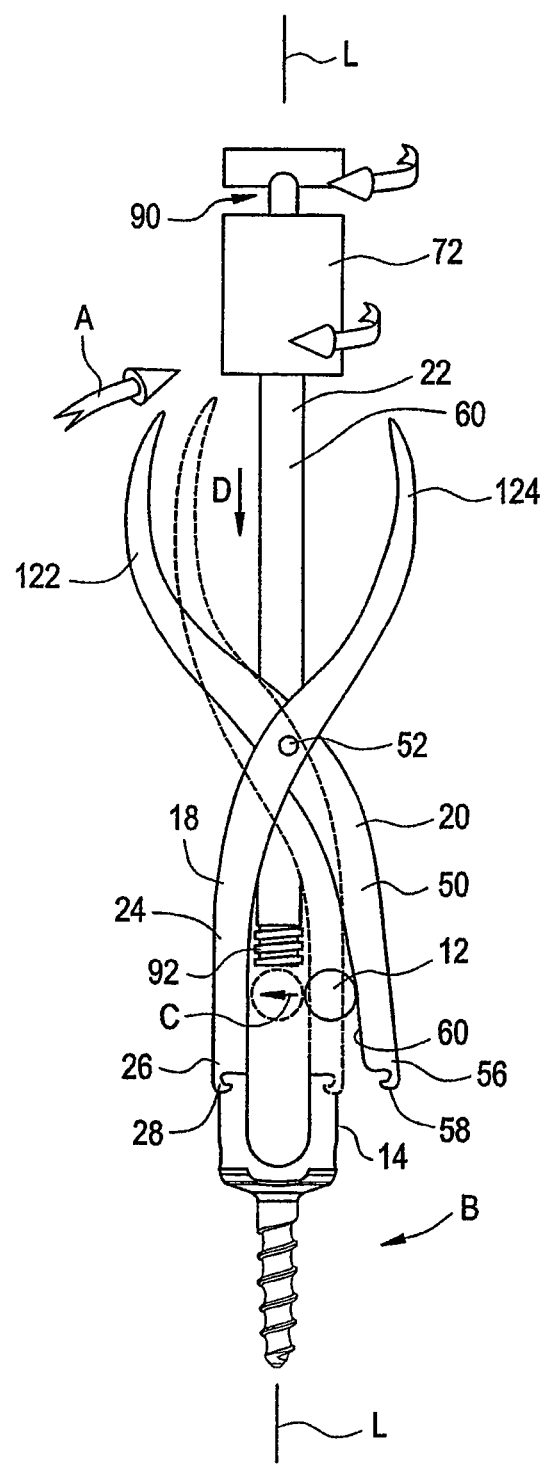
FIG. 13 is a side view of the instrument of FIG. 1, illustrating the operation of the instrument to adjust a spinal fixation element relative to a bone anchor.

The distal end 64 of the tube 60 may indirectly or directly contact the spinal fixation element 12 to adjust the spinal fixation element 12 in the second direction. For example, in the illustrated embodiment, the tube 60 may be advanced with the closure mechanism delivery instrument 90 and the closure mechanism 92 may be positioned distal to the distal end 64 of the tube 60, as illustrated in FIGS. 11B and 13. In such embodiments, the closure mechanism 92 may contact the spinal fixation element 12 and, thus, the tube 60 may adjust the spinal fixation element 12 through the closure mechanism 92. In alternative embodiments, the distal end 64 of the tube 60 may directly contact the spinal fixation element 12 to effect adjustment of the spinal fixation element 12, as illustrated in FIG. 11C. In certain embodiments, the distal end 64 of the tube may be sized and shaped to facilitate contact with the spinal fixation element 12. For example, the distal end 64 may be forked or bifurcated to engage the spinal fixation element 12 on opposing sides, as illustrated in FIG. 11A. In such embodiments, the distal end 64 may have an arcuate contact surface 68 having a curvature approximate to the curvature of the spinal fixation element 12.

The exemplary instrument 10 may include a coupling mechanism 100 that is connected to the first arm 24 and/or the second arm 50 and is configured to receive the second adjustment mechanism 22, e.g., tube 60, and permit motion of the second adjustment mechanism 22 relative to the first arm 24 and/or the second arm 50. In the illustrated embodiment, for example, the coupling mechanism 100 is a collar or nut 102 having internal threads 104 that may engage external threads 70 provided on the tube 60 between the proximal end 62 and the distal end 64 of the tube 60. Rotation of the tube 60 relative to the collar 102 causes the tube 60 to advance distally or proximally, depending on the direction of rotation, relative to the first arm 24 and the second arm 50. The tube 60 may be provided with a handle 72 at the proximal end 62 of the tube 60 to facilitate gripping and rotation of the tune 60.

The collar 102 may be connected to the first arm 24 and/or the second arm 50 anywhere along the length of the arm(s). In the illustrated embodiment, for example, the collar 102 is connected to and positioned between the first arm 24 and the second arm 50. The collar 102 may be positioned between the proximal and distal ends of the first arm 24 and the second arm 50 proximate the area in which the arms intersect. In the illustrated embodiment, for example, the collar 102 is positioned such that the pivot axis 52 intersects the collar 102.

Figure 9:
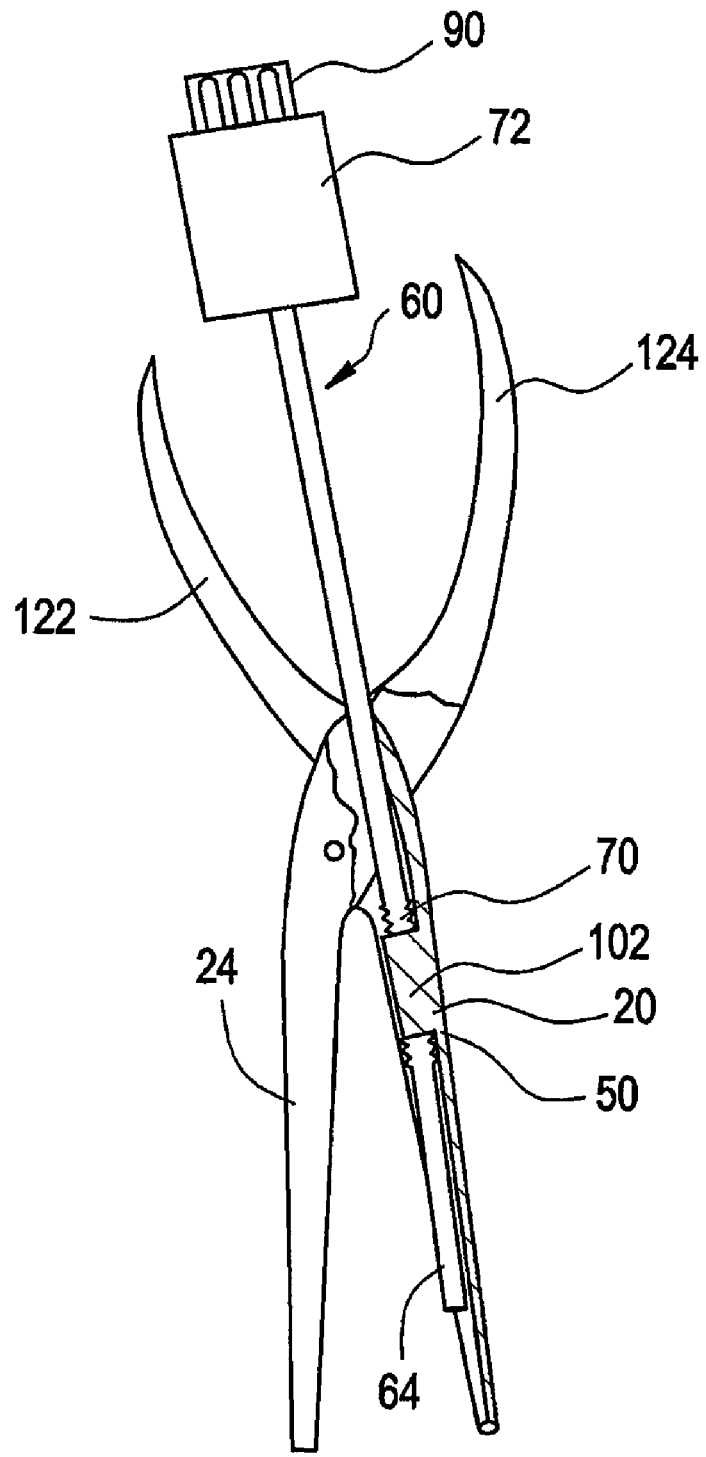
FIG. 9 is a side view of another exemplary embodiment of an instrument for manipulating a spinal fixation element relative to a bone anchor, illustrating the coupling mechanism integrated into an arm of the instrument.

In alternative embodiments, the collar 102 may be integral to the first arm 24 and/or the second arm 50. Referring to FIG. 9, for example, the collar 102 may be integral to the second arm 50 of the instrument 10. Alternatively, the collar 102 may be integral to the first arm 24 or be formed by both the first arm 24 and the second arm 50.

Figure 10:
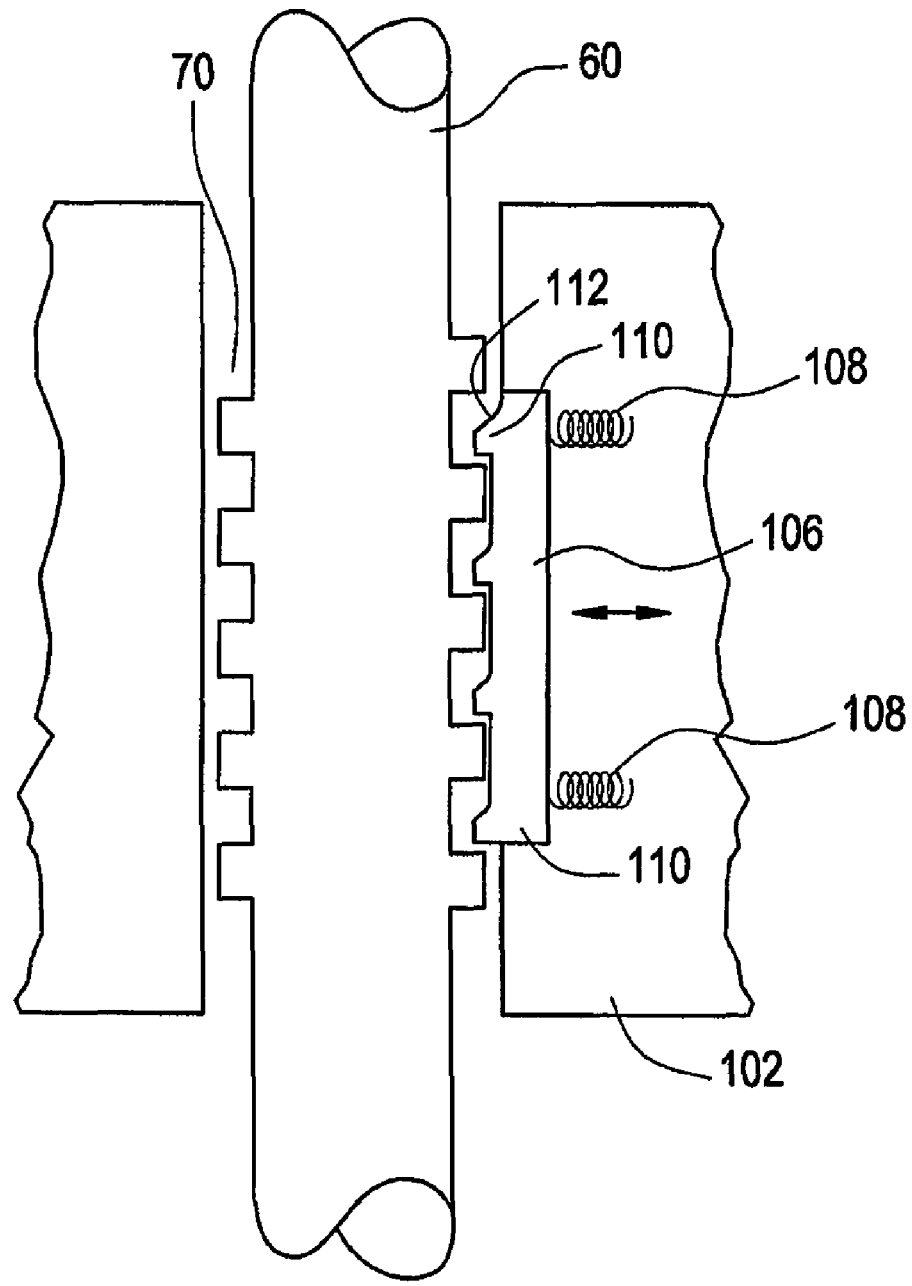
FIG. 10 is a side view of an alternative exemplary embodiment of a coupling mechanism configured to permit motion of the adjustment mechanism relative to the first arm and the second arm of the instrument.

In alternative embodiments, the collar 102 may be configured to allow the tube 60 to advance distally without rotation. For example, the collar 102 may include a threaded member 106 that is movable in a direction perpendicular to the tube 60 to allow the threaded member 106 to selectively engage the threads 70 on the tube 60, as illustrated in FIG. 10. In the illustrated embodiment, the threaded member 106 is movable between a first position in which the threaded member 106 engages the external threads 70 in the tube 60, as illustrated in FIG. 10, and a second position in which the threaded member 106 disengages the external threads 70 on the tube 60 to permit axial motion of the tube 60 without rotation. In this manner, the tube 60 may be quickly advanced, without the need for rotation, into contact with the spinal fixation element 12. Upon engagement with the spinal fixation element 12, the tube 60 may be rotated to engage the threaded 70 on the tube 60 with the threads of the threaded member 106 and, thus, further advance the spinal fixation element 12. The collar 106 may include one or more springs 108 that bias the threaded member 106 into engagement with the threads 70 of the tube 60, i.e., the first position. The teeth 110 of the threaded member 106 may include an angled flank 112 that facilitates translation of the threaded member 106 from the first position to the second position.

The exemplary instrument 10 may include an activation mechanism 120 coupled to the bone anchor grasping mechanism 18 and to the first adjustment mechanism 20 to effect relative motion of the first arm 24 and the second arm 50. For example, the activation mechanism 120 may comprise a first handle 122 connected and proximal to the first arm 24 and a second handle 124 connected and proximal to the second arm 50. The first handle 122 may be pivotally connected to the second handle 124. Motion of the first handle 122 and the second handle 124 towards one another causes the distal end 26 of the first arm 24 to move toward the distal end 56 of the second arm 50. The activation mechanism 120 may include a spring or the like positioned between the first handle 122 and the second handle 124 to bias the first handle 122 and the second handle 124 to an open, separated position. The activation mechanism 120 may also include a locking mechanism, such as a latch or a ratchet assembly, that is operable to lock the handles 122, 124 in position relative to one another, for example, in a closed position to retain the bone anchor between the distal ends 26, 56 of the arms 24, 50.

Although the exemplary activation mechanism 120 includes two handles 122, 124, in other exemplary embodiments, the activation mechanism 120 may include additional pivotally connected linkages to increase the mechanical advantage provided by the activation mechanism.

In the exemplary embodiment, the handles 122, 124 of the activation mechanism 120 are oriented generally in a direction parallel to the longitudinal axis L of the instrument 10. In alternative embodiments, the activation mechanism 120 may comprise a fixed handle 130 and a movable handle 132 that is pivotally connected to the fixed handle 130 at a pivot point 134 proximal to the pivot axis 52 of the first arm 24 and the second arm 50, as illustrated in FIG. 7. In the exemplary embodiment illustrated in FIG. 7, motion of the movable handle 132 toward the fixed handle 130 causes the causes the distal end 66 of the second arm 50 to move toward the distal end 26 of the first arm 24. The movable arm 132 may be connected to the second arm 50 by one or more pivotally connected linkages.

In alternative embodiments, the one or more of the handles of the activation mechanisms 120 may be laterally oriented relative to the longitudinal axis L of the instrument 10. Referring to FIG. 8, for example, a movable handle 132 and a fixed handle 130 may be oriented lateral to, e.g., at angle to, the longitudinal axis L of the instrument 10. In the embodiment illustrated in FIG. 8, for example, the movable handle 132 and the fixed handle 130 are oriented generally perpendicular to the longitudinal axis L of the instrument 10.

The components of the exemplary instrument 10 may be made from any material suitable for use in vivo, including, for example, metals such as stainless steel and titanium, polymers, or composites thereof. The components of the exemplary instrument 10 may be constructed of the same or different materials.

In use, the exemplary instrument 10 may be employed to adjust the position of a spinal fixation element 12 in multiple directions relative to a bone anchor. Referring to FIG. 13, the distal end 26 of the first arm 24 may be engaged with the bone anchor 14. By moving the second handle 122 toward the first handle 124, in the direction of arrow A, the distal end 56 of the second arm 50 is pivoted about the pivot axis 52 and moved in the direction of the distal end 26 of the first arm 24 and the bone anchor 14, as indicated by arrow B. As the second arm 50 moves toward the bone anchor 14, the inner surface 60 of the second arm 50 engages the spinal fixation element 12 to move the spinal fixation element 12 in a first direction, indicated by arrow C, toward the bone anchor 14. This is generally referred to as lateral approximation of the spinal fixation element 12.

Upon vertical alignment of the spinal fixation element 12 with the longitudinal axis L of the instrument and the bone anchor, the tube 60 may be advanced distally in a second direction into contact with spinal fixation element 12, as indicated by arrow D. Further advancement of the tube 60 toward the bone anchor 14 advances the spinal fixation element 12 toward the bone anchor 14 until the spinal fixation element 12 is seated in the bone anchor 14. The delivery instrument 90 may used to engage the closure mechanism 92 with the bone anchor 14 and secure the spinal fixation element 12 to the bone anchor 14.

FIGS. 14-17 illustrate another alternative embodiment of an instrument 210 for manipulating a spinal fixation element, which is particularly suited to adjust a spinal fixation element in two directions relative to a bone anchor. For example, the instrument 210 is suited for both lateral adjustment of the spinal fixation element and vertical adjustment of the spinal fixation element relative to the bone anchor. The instrument 210 includes a bone anchor grasping mechanism 218 configured to engage a first receiving portion of the bone anchor in the manner described above in connection with other embodiments as illustrated in FIGS. 2-6, 12A-12D, and 13. Instrument 210 also includes a first adjustment mechanism 220 operable to adjust the spinal fixation element in a first direction relative to the bone anchor, and a second adjustment mechanism 222 operable to adjust the spinal fixation element in a second direction, at an angle to the first direction, e.g., generally perpendicular to the first direction, relative to the bone anchor. As will be described below, the first adjustment mechanism 222 can have first and second arms 224, 250 that are connected together at a pivot and which are operable in a pliers-like manner.

As illustrated and in the description of the instrument 210 that follows, the spinal fixation element is a spinal rod 12 and the bone anchor is a monoaxial bone screw 14 as described above in connection with other embodiments. However, one skilled in the art will appreciate that the spinal fixation element and the bone anchor are not limited to the illustrated embodiments and that the instrument may be used with any type of spinal fixation element and any type of bone anchor.

Figure 14:
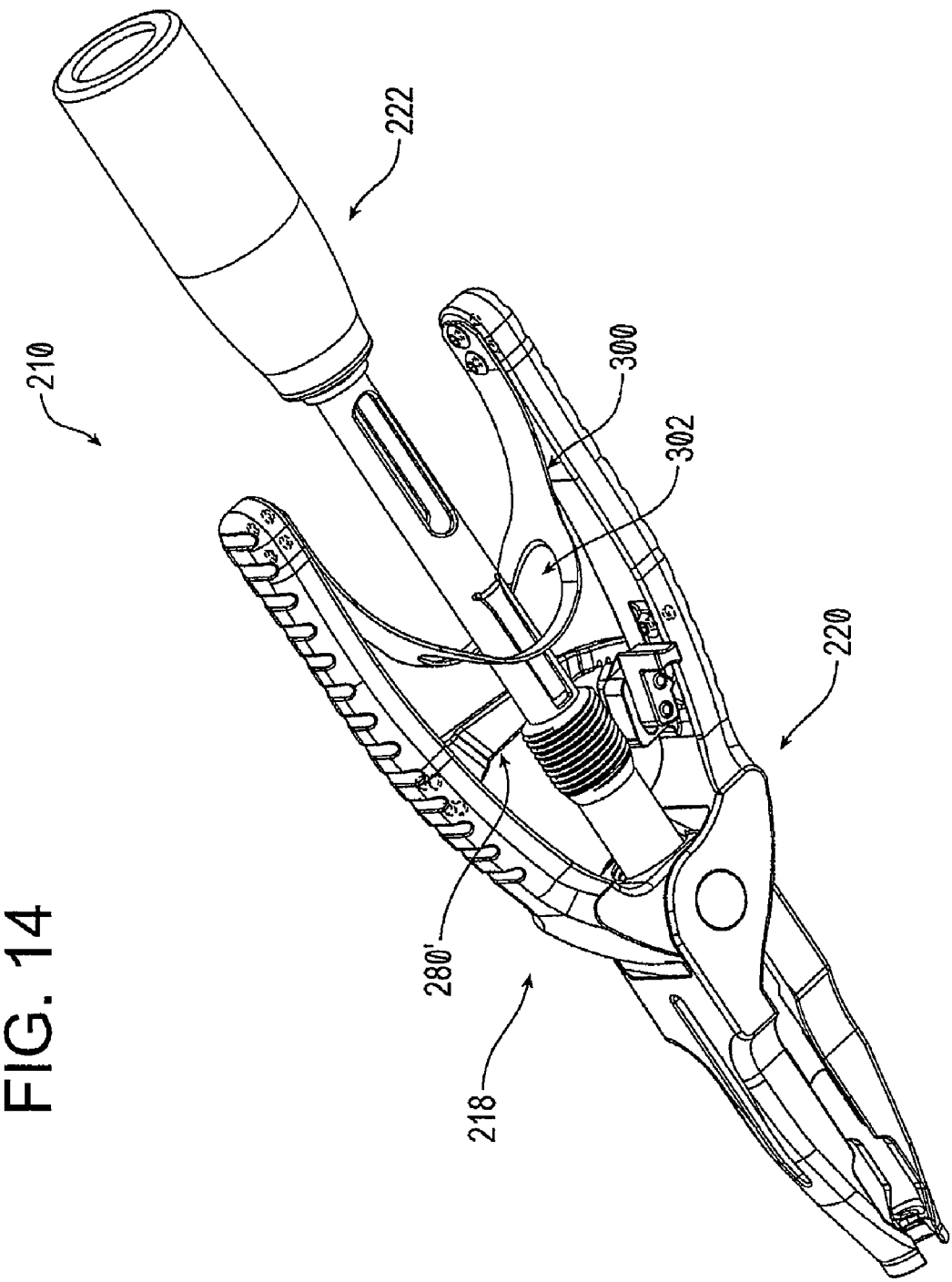
FIG. 14 is a front perspective view of another exemplary embodiment of an instrument for manipulating a spinal fixation element relative to a bone anchor.
Figure 15A:
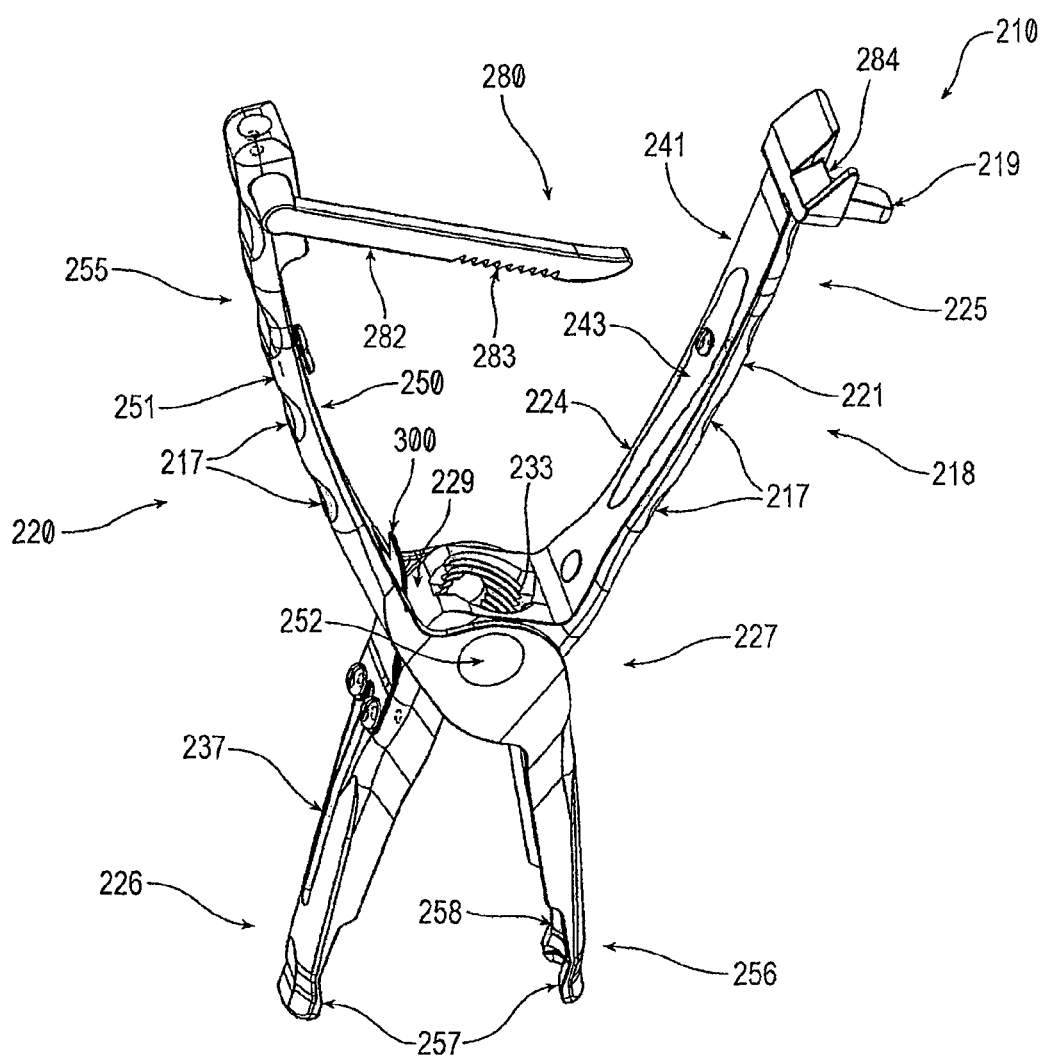
FIG. 15A is a back perspective view of another exemplary embodiment of an instrument for manipulating a spinal fixation element relative to a bone anchor, with a second adjustment mechanism removed and in a position where a rack is not engaged with a pawl.
Figure 15B:
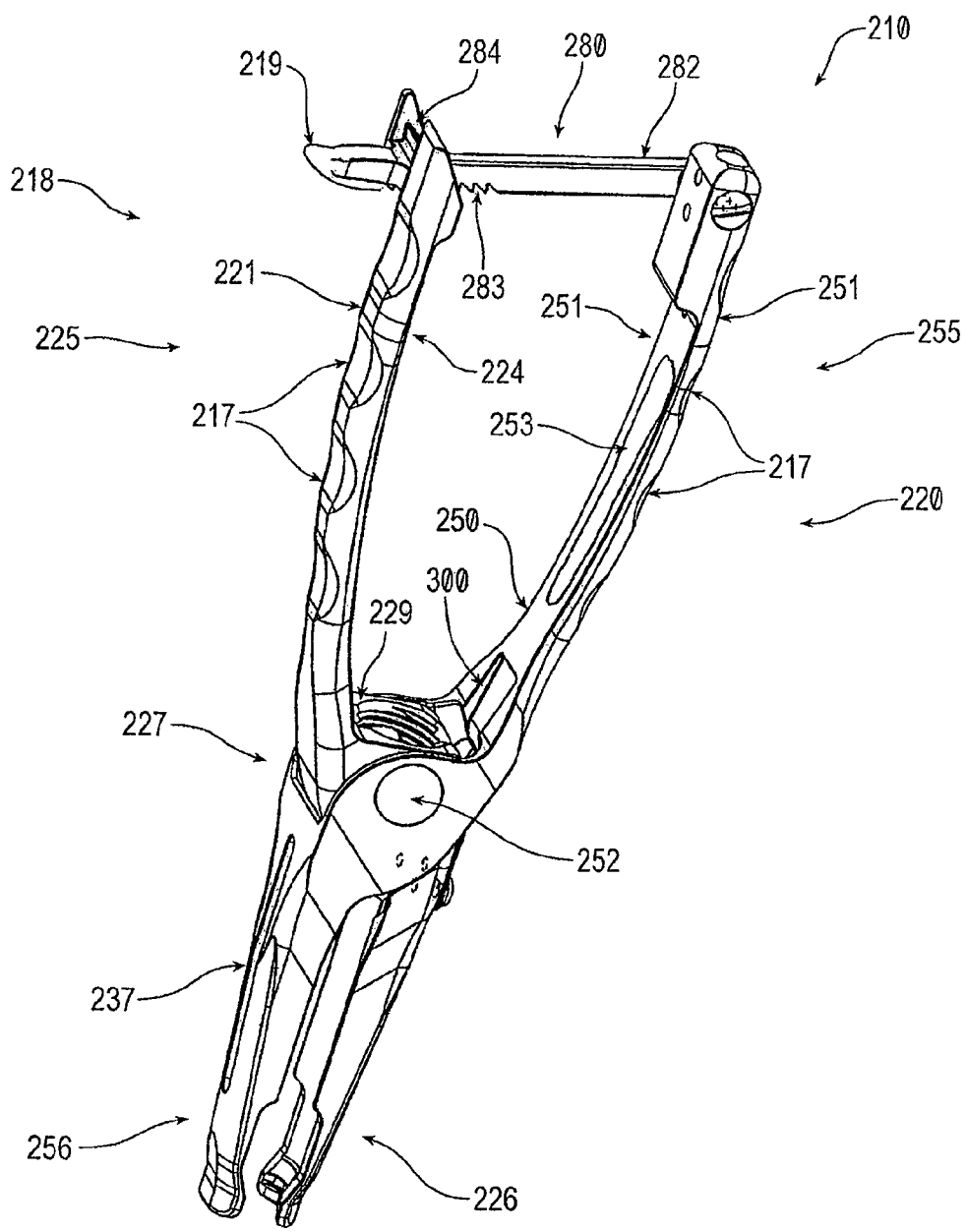
FIG. 15B is a front perspective view of the instrument of FIG. 15A in a position where the rack is engaged with the pawl.
Figure 15C:
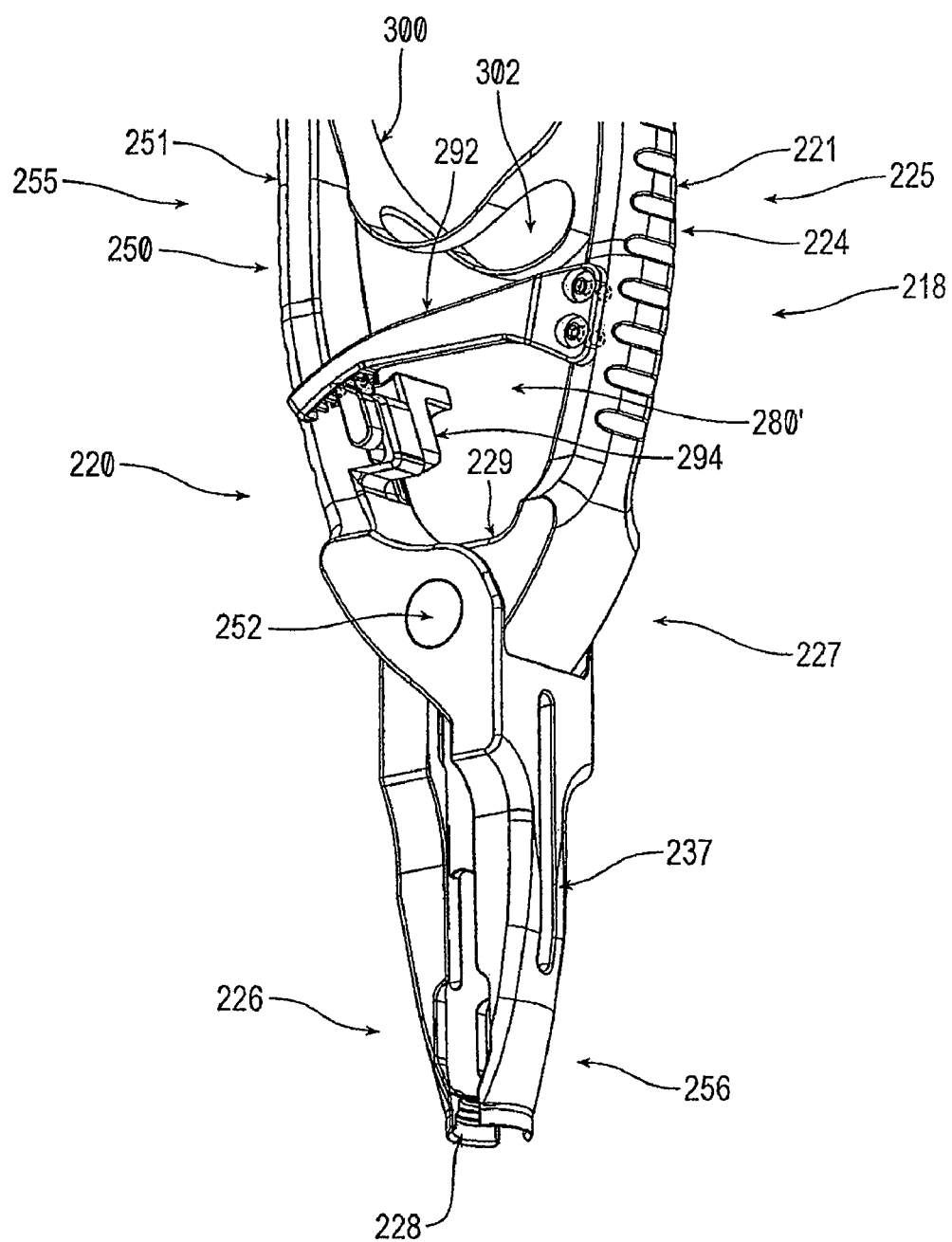
FIGS. 15C and 15D are partial back and front perspective views of an alternative embodiment of the instrument of FIG. 15A, illustrating an alternative locking mechanism.
Figure 15D:
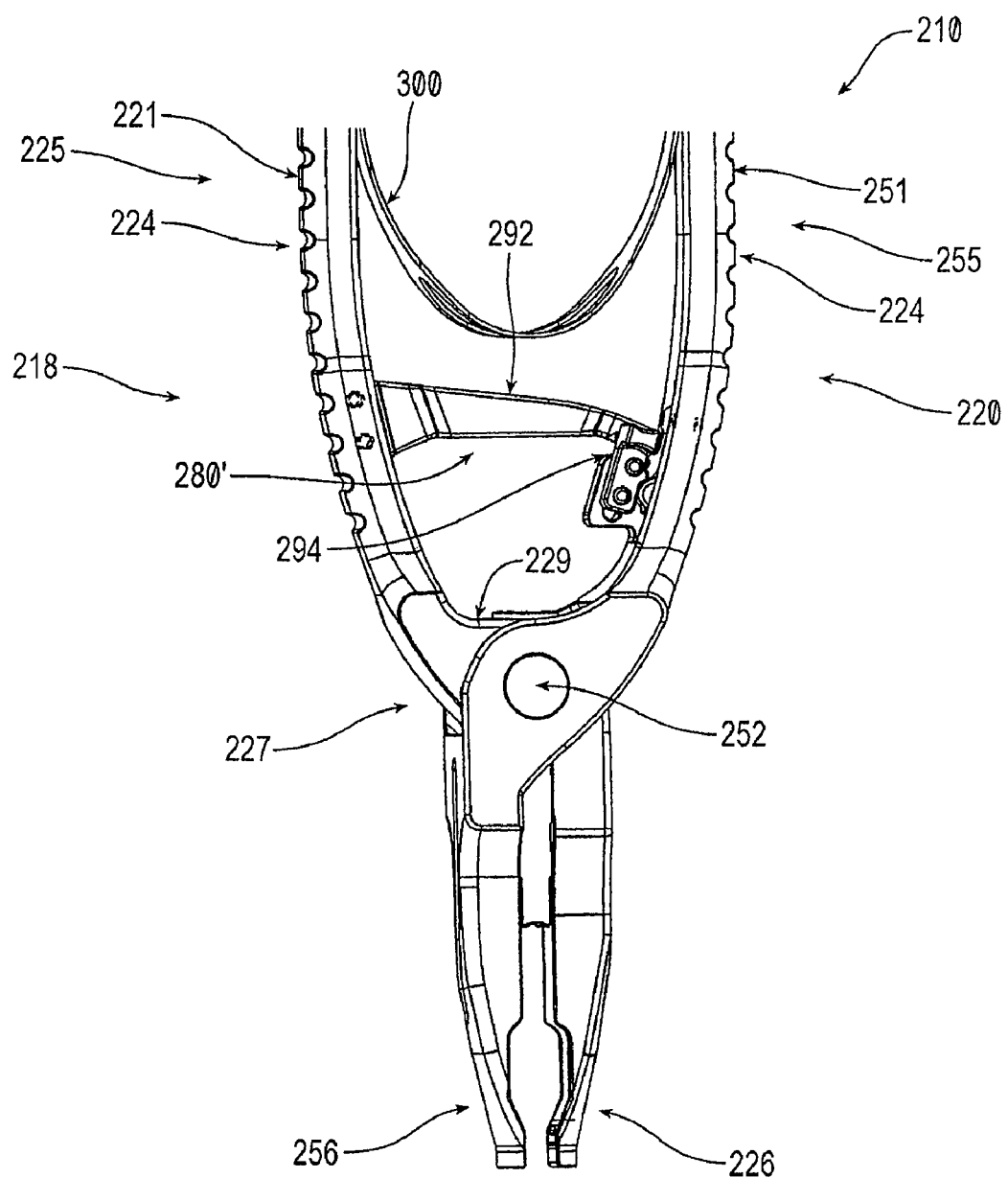
Figure 16:
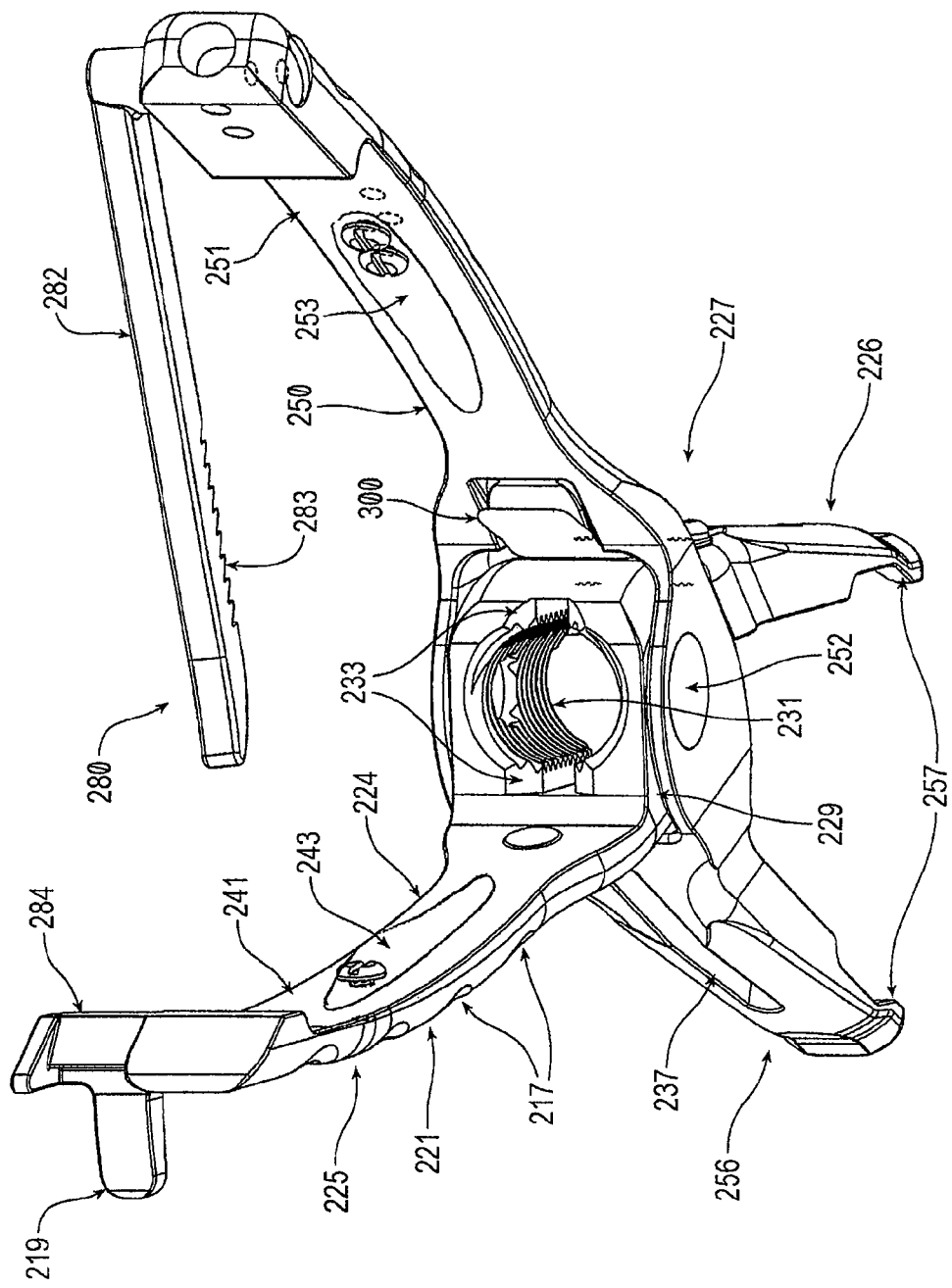
FIG. 16 is a top perspective view of the instrument of FIG. 15A.

Referring to FIGS. 14-16, the bone anchor grasping mechanism 218 of the instrument 210 may include a first arm 224 having a proximal end 225 with a handle portion 221, a distal end 226 configured to releasably engage the bone anchor, and an intermediate portion 227 disposed between the proximal end 225 and the distal end 226. The first arm 224 may engage and disengage a bone anchor in a manner similar to the manner described above for the first arm 24 of the instrument 10, or in any other manner known to one skilled in the art.

In one embodiment of the instrument 210, the handle portion 221 of the first arm 224 may include features that would assist in the comfort and ease of use of the instrument 210. Any number of features could be included to provide such comfort and ease of use. In one embodiment illustrated in FIGS. 15A, 15B, and 16, the first arm 224 includes finger grips 217, which are represented by contours or depressions formed in the handle portion 221. In an alternative embodiment, the finger grips 217 and/or the handle portion 221 may be cushioned. In yet another embodiment, the proximal end 225 of the first arm 224 may include a finger stop 219. As illustrated in FIGS. 15A, 15B, and 16, the finger stop 219 is formed by a flange or lateral extension and eases use by assisting in locating the proximal end 225 of the first arm 224. One skilled in the art will appreciate that a variety of different features to assist in the comfort and ease of use of the instrument 210 can be used, and that the examples of finger grips and a finger stop are merely two examples.

In yet another embodiment, the distal end 226 of the first arm 224 may be configured to engage a first receiving portion provided in the bone anchor. For example, the distal end 226 of the first arm 224 may include one or more radially inward facing projections 228 that are sized and shaped to seat within the first receiving portion provided in the bone anchor, e.g., as shown in FIG. 6. In another embodiment, the bone anchor may contain multiple receiving portions, such that the distal end 226 of the first arm 224 includes multiple projections 228 to engage the multiple receiving portions.

In an exemplary embodiment, the intermediate portion 227 may include a housing 229, which can have a threaded bore 231 formed therein. The housing may be oriented in a plane that is generally transverse to the orientation of the first arm 224, and one or more alignment slots 233 may be formed in the housing 229 in communication with the threaded bore 231. The shape of the alignment slots 233 may vary as long as they form a shape that is effective to assist in aligning the second adjustment mechanism 222 with the bone anchor grasping mechanism 218 to facilitate coupling of the second adjustment mechanism 222 to the threaded bore 231 as will be described below. A further alignment feature may be provided on an inner portion of the first and/or second arm 224, 250 in the form of an alignment groove 237 that is in communication with the alignment slot 233 of the housing 229. In one embodiment, both the first and second arms 224, 250 include the alignment groove 237. It is envisioned that any number of alignment grooves 237 can be used in the instrument 210. It is also envisioned that the shape of the alignment grooves 237 is not limited to the shape illustrated in FIGS. 14-16, but rather the shape can be any shape that assists in maintaining alignment of the second adjustment mechanism 222 with the bone anchor grasping mechanism 218 as it moves relative to the first adjustment mechanism 220.

The first adjustment mechanism 220 also includes a second arm 250 that is pivotally connected to the housing 229 of the first arm 224 and that is operable to adjust the spinal fixation element in a first direction upon pivoting of the second arm 250 relative to the first arm 224. For example, the first arm 224 may be directly pivotally connected to the second arm 250 such that the first and second arms 224, 250 pivot about a pivot axis 252 that intersects the first and second arms 224, 250. In alternative embodiments, the first and second arms 224, 250 may pivot in alternative manners, such as those manners described above and illustrated in FIGS. 7 and 8 for the instrument 10.

The second arm 250 may include a proximal end 255 with a handle portion 251 and a distal end 256 configured to releasably engage the bone anchor. In alternative embodiments, any feature that would assist in the comfort and ease of use of the instrument 210, such as the finger grips 217 and the finger stop 219 provided on the first arm 224 as described above, may also be provided on the second arm 250. Additionally, the distal end 256 of the second arm 250 may be configured in a manner analogous to the distal end 226 of the first arm 224. For example, the distal end 256 of the second arm 250 may include a projection 258 that is sized and shaped to engage a second receiving portion in the bone anchor. In another embodiment, the bone anchor may contain multiple receiving portions, such that the distal end 256 of the second arm 250 includes the multiple projections 258 to engage the multiple receiving portions. Furthermore, the distal end 226 of the first arm 224 and/or the distal end 256 of the second arm 250 may include features that allow for easier and more precise movement of the spinal fixation element relative to the bone anchor. In one embodiment the feature is a guiding portion 257 (FIG. 15A) that is angled toward the other of the first arm 224 and the second arm 250 respectively. It is envisioned that any number of features that provide for easier and more precise movement of the spinal fixation element relative to the bone anchor may be incorporated to the distal ends 226, 256 of the first and second arms 224, 250, respectively.

In one aspect, the instrument 210 can be constructed such that one or both of the first and second arms 224, 250 are sufficiently thin so as to create an inherent flexibility within the first and second arms 224, 250. This design enables the first and second arms 224, 250 to store potential energy as a result of a further closure force applied to either or both of the handle portions 221, 251 after the distal ends 226, 256 of the first and second arms 224, 250, respectively, are engaged with the bone anchor. In one embodiment, the handle portion 251 of the second arm 250 is able to move a distance in the range of approximately 5 to 10 millimeters toward the handle portion 221 of the first arm 224 after the distal ends 226, 256 of the first and second arms 224, 250, respectively, are engaged with the bone anchor. One skilled in the art will appreciate that in alternative embodiments, the handle portion 221 of the first arm 224 may be able to move a distance in the range of approximately 5 to 10 millimeters toward the handle portion 254 of the second arm 240, or alternatively, that both handle portions 221, 251 may be able to move a distance in the range of 5 to 10 millimeters toward each other after the distal ends 226, 256 of the first and second arms 224, 250, respectively, are engaged with the bone anchor. One skilled in the art will appreciate that the first and second arms 224, 250 can be constructed in a variety of different ways, and with differing relative dimensions, to achieve such desired flexibility. For example, the thickness of the arms can be greater at a distal end and gradually decrease in the proximal direction. In one embodiment, the first and second arms 224, 250 are constructed such that the thickness of the arms at their distal ends is approximately 5 mm, the thickness of the arms at an intermediate portion is approximately 4 mm, and the thickness of the arms at their proximal ends is approximately 3 mm.

One skilled in the art will appreciate that it is possible to create such inherent flexibility in the instrument 210 in other ways as well. For instance, by way of a non-limiting example, and as shown in FIGS. 15A, 15B, and 16, a channel 243 and a channel 253 may be disposed on an inner surface 241 of the first arm 224 and an inner surface 251 of the second arm 250, respectively. Similar to sufficiently thin arms, the channels 243, 253 both create an inherent flexibility within the first and second arms 224, 250, respectively, such that the first and second arms 224, 250 are enabled to store potential energy as a result of a further closure force applied to either or both of the handle portions 221, 251 after the distal ends 226, 256 of the first and second arms 224, 250, respectively, are engaged with the bone anchor. Only one channel 243, 253 is necessary to create inherent flexibility in the instrument 210. One skilled in the art will appreciate that the size and shape of channels 243, 253 may vary as long as they are of a size and/or shape that assists in creating inherent flexibility.

The bone anchor grasping mechanism 218 may include a biasing mechanism 300 configured to bias at least one of the handle portions 221, 251 of the first and second arms 224, 250, respectively, to either an open position or a closed position. In one embodiment, the biasing mechanism 300 may be disposed between the handle portions 221, 251. In another embodiment, the biasing mechanism 300 may be disposed between the intermediate portion 227 of the first arm 224 and the second arm 250. The biasing mechanism 300 can take a variety of forms, but in one embodiment it is a leaf spring. In another embodiment, the biasing mechanism 300 may have a central opening 302 formed therein that is configured to permit passage of the second adjustment mechanism 222 therethrough. In yet another embodiment, the biasing mechanism 300 may include two or more components which cooperate with one another to form the biasing mechanism 300. One skilled in the art will appreciate that a variety of different biasing mechanisms can be used with the bone anchor grasping mechanism 218, and that the example of a leaf spring is merely one example.

In addition to including the biasing mechanism 300, the bone anchor grasping mechanism 218 may also include a locking mechanism 280 coupled to the handle portion 251 of the second arm 250 that is effective to maintain the handle portions 221, 251 in a desired position relative to one another. FIGS. 15A and 15B illustrate one example of a locking mechanism 280 that includes a rack 282, with teeth 283 formed therein, that is pivotally mounted on the handle portion 251 of the second arm 250 such that the rack 282 extends towards the first arm 224. In this embodiment, a pawl 284 may be formed on the handle portion 221 of the first arm 224 such that the rack 282 is able to selectively engage the teeth 283 with the pawl 284 to resist the force of the biasing mechanism and thus maintain a desired position of the handle portions 221, 251.

Various design modifications are possible. For example, the teeth 283 may be recessed in order to prevent undesired cutting of items such as surgical gloves. Further, when the rack 282 is selectively disengaged from the pawl 284, it may be pivotably oriented at an angle other than zero relative to a plane of the handle portions 221, 251. One skilled in the art will appreciate that the locking mechanism 280 could be coupled to either of the handle portions 221, 251.

Just as the locking mechanism 280 may be coupled to either of the handle portions 221, 251, the locking mechanism 280 may also be coupled to any portion of either the first or second arm 224, 250, including the intermediate portion 227 of the bone anchor grasping mechanism 218.

FIGS. 15C and 15D illustrate an embodiment of the bone anchor grasping mechanism 218 with an alternative locking mechanism 280'. As illustrated, locking mechanism 280' includes a bar 292 coupled to the first arm 222 and extending towards the second arm 250. A latch 294 is coupled to the second arm 250 such that the latch 294 can selectively engage the bar 292 at various locations across the bar 292 to maintain the handle portions 221, 251 in a desired position relative to one another. A person skilled in the art would recognize that in alternative embodiments, components of the locking mechanisms 280 and 280' such as the rack 282, the pawl 284, the bar 292, and the latch 294 may be located anywhere on the first or second arm 224, 250, depending on the desired operation of the bone anchor grasping mechanism 218. One skilled in the art also will appreciate that a bone anchor grasping mechanism utilizing a rack and a pawl and a bone anchor grasping mechanism utilizing a bar and a latch are just two of many different locking mechanisms that could be used to maintain the handle portions 221, 251 in a desired position relative to one another.

Figure 17:
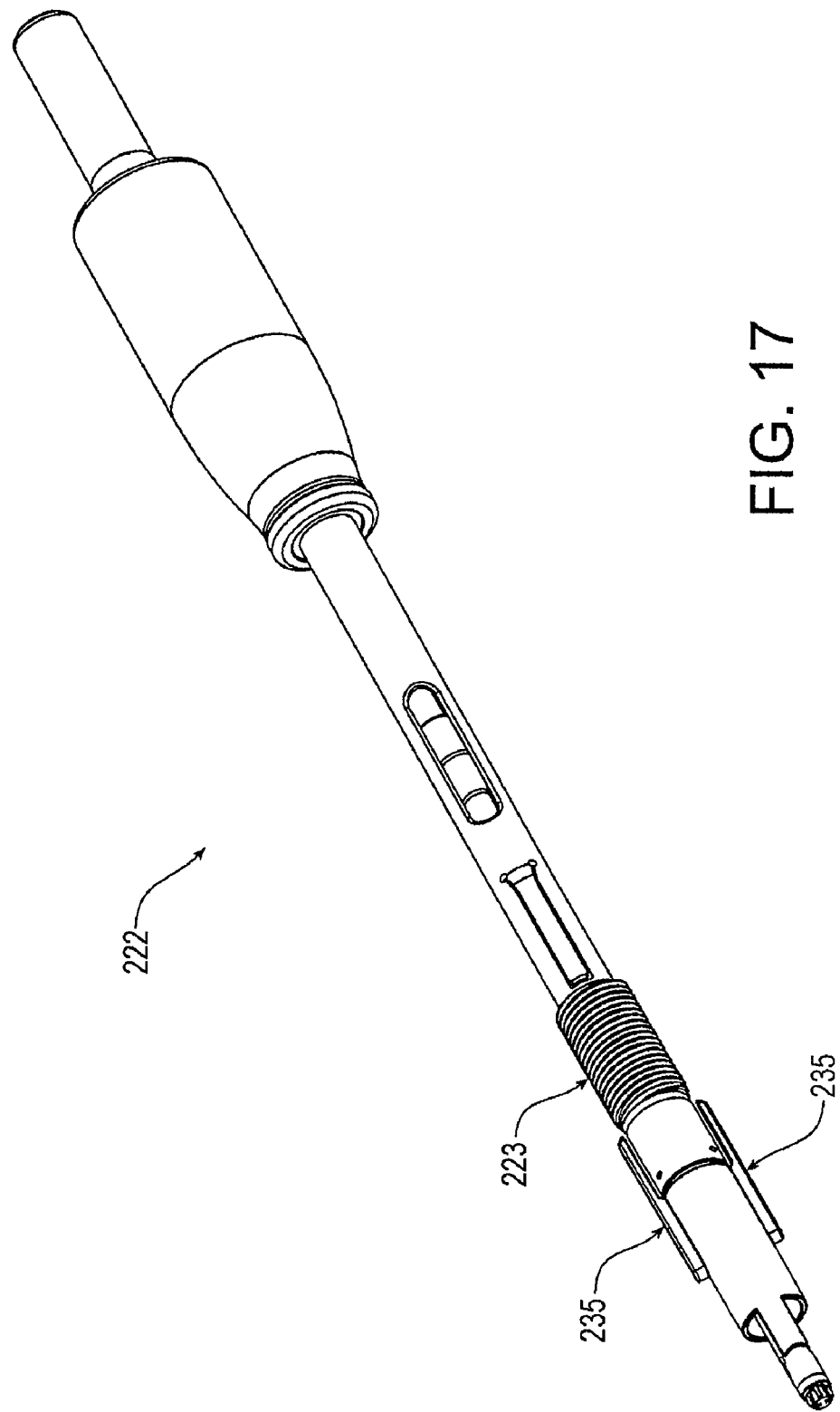
FIG. 17 is a front perspective view of the second adjustment mechanism for use with the instrument of FIGS. 14.

Now referring to FIGS. 14 and 17, the second adjustment mechanism 222 may have a threaded portion 223 formed over at least a portion thereof that is configured to be removably and replaceably mated with the threaded bore 231 of the housing 229. In one embodiment the threaded portion 223 is disposed on an intermediate portion of the second adjustment mechanism 222. The second adjustment mechanism 222 can also include an alignment feature 235 that is distal to the threaded portion 223 and configured to fit within the alignment slot 233 of the housing 229 and the alignment groove 237 of the first or second arm 224, 250. The alignment feature can be one or more projections formed on an outer surface of the second adjustment mechanism 222 that is able to fit within the alignment slot(s) 233 and the alignment groove(s) 237. In one embodiment, the alignment feature 235 may be a fin, but it can also be a pin or other protruding structure capable of communicating with the alignment slot(s) 233 and the alignment groove(s) 237. While FIG. 17 illustrates the second adjustment mechanism 222 having two opposed alignment features 235, it is envisioned that one or more than two alignment features 235 can be present on the second adjustment mechanism 222.

The second adjustment mechanism 222 may also be movable relative to the first and/or second arm 224, 250 to adjust the spinal fixation element relative to the bone anchor in a second direction that is different to, e.g., at an angle to, the first direction. In use, the second adjustment mechanism 222 can be aligned for placement within the threaded bore 231. When a biasing mechanism such as the biasing mechanism 300 as shown in FIG. 14 is present, the second adjustment mechanism passes through the central opening 302 and into the threaded bore 231. To pass through the threaded bore 231, the alignment feature 235 must be aligned with the alignment slot(s) 233 and the alignment groove(s) 237. The second adjustment mechanism 222 can be advanced through the threaded bore 231 without rotation until the threaded portion 223 abuts threads of the threaded bore 231. Thereafter, rotation of the second adjustment mechanism 222 allows the threads to mate and further distally advance the second adjustment mechanism 222. The engagement of the threaded portion 223 within threaded bore 231 maintains alignment of the second adjustment mechanism 222 during an initial phase of its distal advancement. The interaction of the alignment feature 235 and the alignment groove(s) 237 maintains alignment upon further distal advancement. One skilled in the art will appreciate that because the second adjustment mechanism 222 is removable, the bone anchor grasping mechanism 218 and the second adjustment mechanism 222 may be used either independently or together.

FIGS. 18-21 illustrate an alternative embodiment of an instrument 310 for manipulating a spinal fixation element, which is particularly suited to adjust a spinal fixation element in two directions relative to a bone anchor. For example, the instrument 310 is suited for both lateral adjustment of the spinal fixation element and vertical adjustment of the spinal fixation element relative to the bone anchor. The instrument 310, which has a forceps-like configuration, includes a first arm 324 configured to engage a first receiving portion in the bone anchor in the manner described above in connection with other embodiments as illustrated in FIGS. 2-6, 12A-12D, and 13. Instrument 310 also includes a second arm 350 pivotally connected to the first arm 324 such that at least one of the first arm 324 and the second arm 350 may be operable to adjust the spinal fixation element in a first direction relative to the bone anchor, a housing 329 coupled to at least one of the first and second arms 324, 350, and a separate adjustment mechanism 322 operable to adjust the spinal fixation element in a second direction, at an angle to the first direction, e.g., generally perpendicular to the first direction, relative to the bone anchor.

As illustrated and in the description of the instrument 310 that follows, the spinal fixation element is a spinal rod 12 and the bone anchor is a monoaxial bone screw 14. One skilled in the art will appreciate that the spinal fixation element and the bone anchor are not limited to the illustrated embodiments. The instrument may be used with any type of spinal fixation element and any type of bone anchor.

Figure 18:
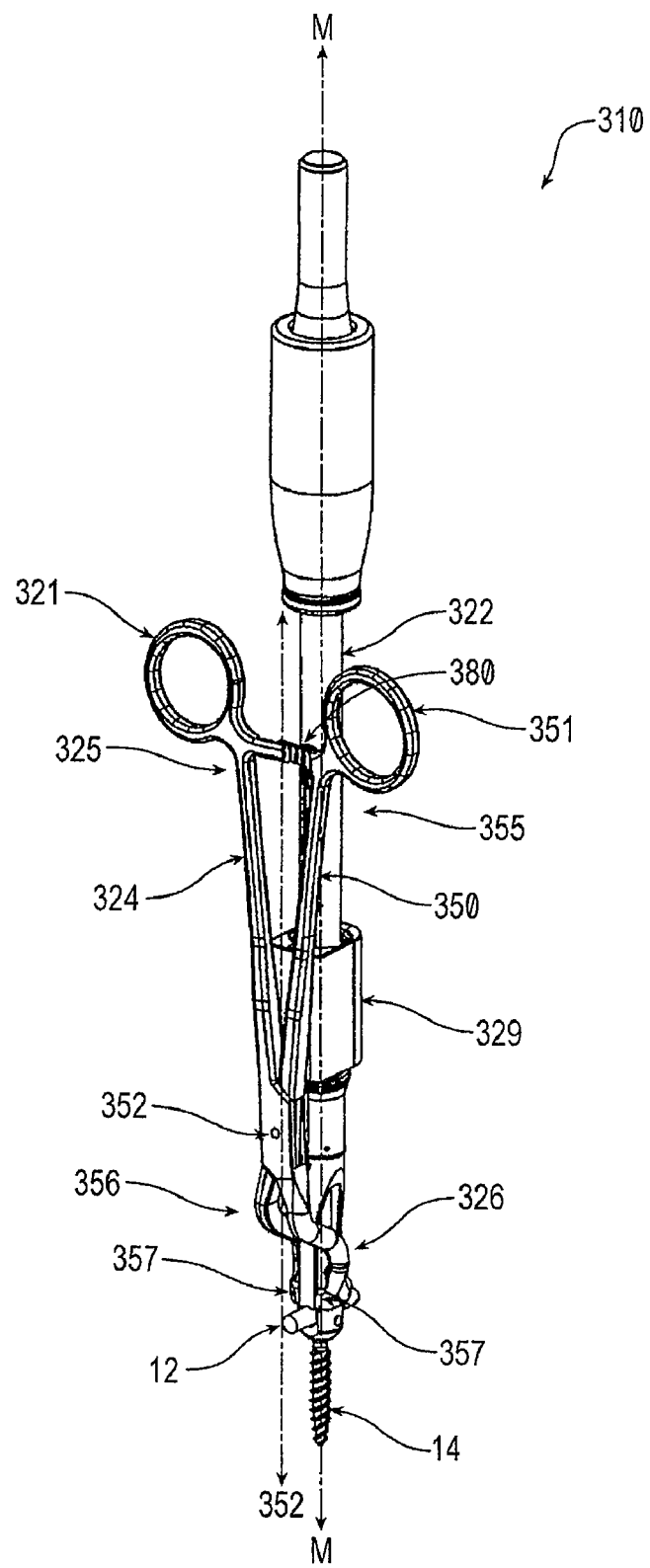
FIG. 18 is a side perspective view of another exemplary embodiment of an instrument for manipulating a spinal fixation element relative to a bone anchor with a separate adjustment mechanism disposed in a housing, illustrating the housing coupled to at least one of a first arm and a second arm.
Figure 19:
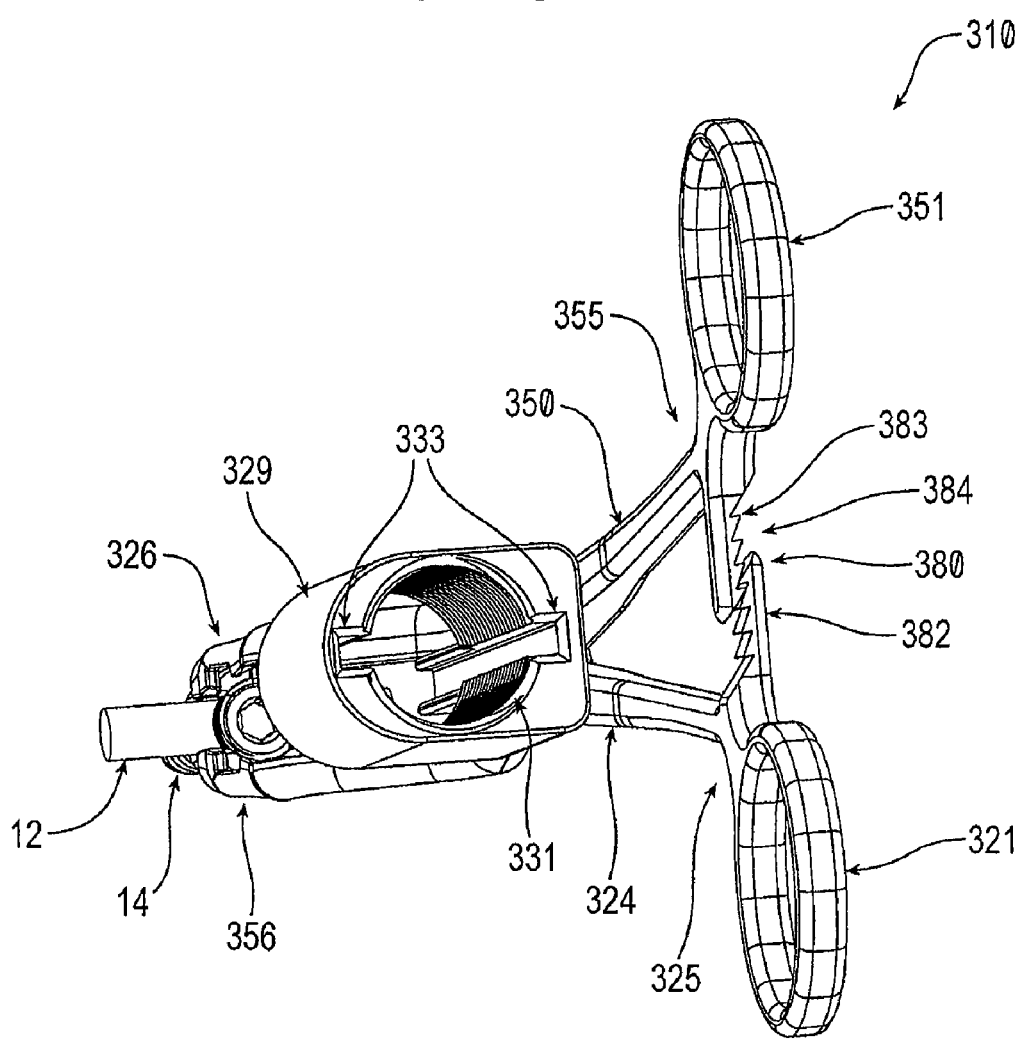
FIG. 19 is a top perspective view of the instrument of FIG. 18, with the separate adjustment mechanism removed.
Figure 20:
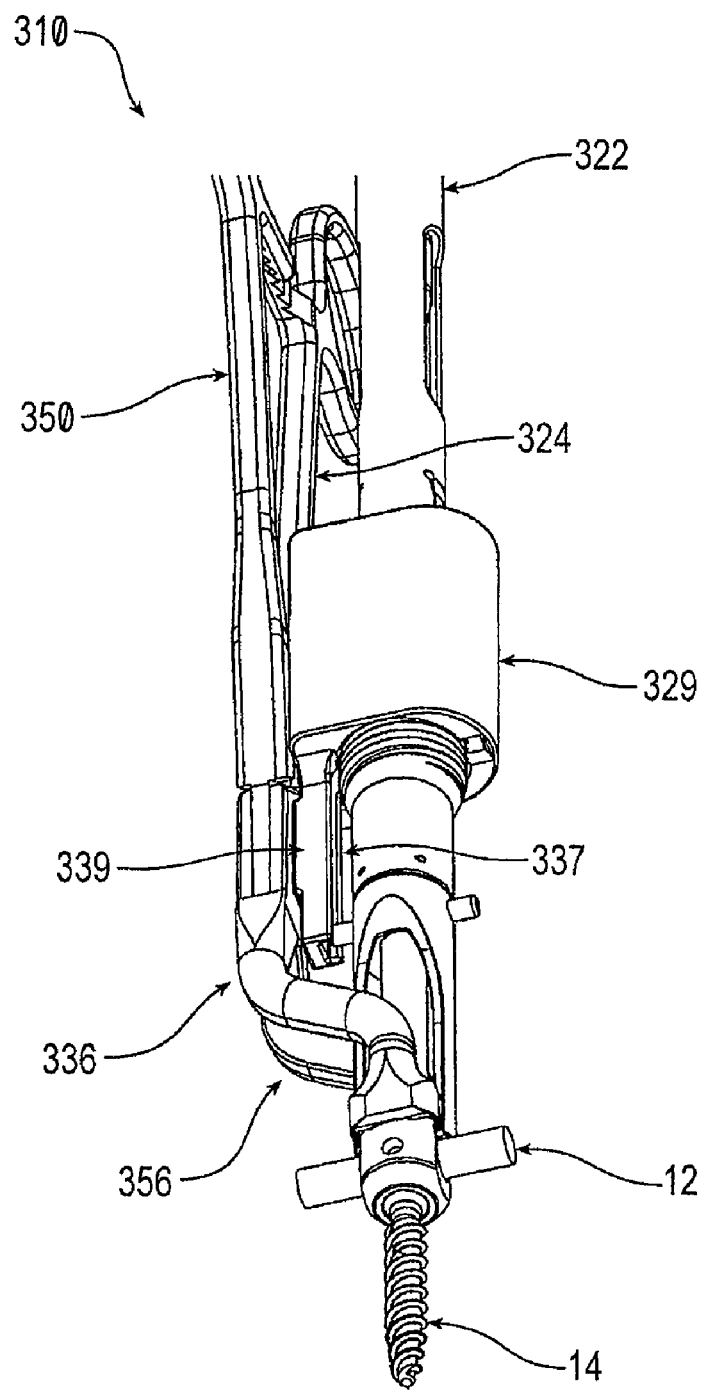
FIG. 20 is a front perspective view of the housing of the instrument of FIG. 18, illustrating the coupling of the housing to one of the first arm and the second arm.

Referring to FIGS. 18-20, the first arm 324 may include a proximal end 325 with a handle portion 321 (e.g., a finger or thumb loop) and a distal end 326 configured to releasably engage the bone anchor. The first arm 324, and in particular the distal end 326, may engage and disengage a bone anchor in a manner similar to the manner described above for the instrument 10, or in any other manner known to one skilled in the art.

The second arm 350 may be pivotally connected to the first arm 324 and at least one of the first and second arms 324, 350 is operable to adjust the spinal fixation element in a first direction upon pivoting relative to the other arm. For example, the first arm 324 may be directly pivotally connected to the second arm 350 such that the first and second arms 324, 350 pivot about a pivot axis 352 that intersects the first and second arms 324, 350. The first and second arms 324, 350 may pivot in alternative manners, such as those manners described above and illustrated in FIGS. 7 and 8 for the instrument 10.

The second arm 350 may include a proximal end 355 with a handle portion 351 (e.g., a finger or thumb loop) and a distal end 356 configured to releasably engage the bone anchor. The distal end 356 of the second arm 350 may be configured in a manner that is analogous to the distal end 326 of the first arm 324 and similar to the distal end 256 of the instrument 210, including features such as a receiving portion(s) and a guiding portion 357 that is configured and operates similar to the angled guiding portion 257 of the instrument 210. Similarly, the first and/or second arms 324, 350, may be manufactured in a manner similar to that described above for the first and second arms 224, 250 to create an inherent flexibility within the first and second arms 324, 350 as described above.

As shown in FIGS. 18-20, the first and second arms 324, 350 each have a somewhat curved structure such that the distal ends 326, 356 of the first and second arms 324, 350 are longitudinally offset from the proximal ends 325, 355 of the first and second arms 324, 350. Meanwhile, the housing 329 is coupled to at least one of the first and second arms 324, 350 and may include a threaded bore 331. In one embodiment, the housing 329 is positioned alongside and offset from a longitudinal axis of the proximal ends 325, 355 of the first and second arms 324, 350. In addition, the housing is proximal to and longitudinally aligned with the distal ends 326, 356 of the first and second arms 324, 350. Such an orientation creates an alignment such that a longitudinal axis M running through a center of the threaded bore 331 extends between the distal ends 326, 356 of the first and second arms 324, 350, and is generally parallel to at least one of the handle portions 321, 351.

The components of the housing 329 are similar to the housing 229 of the instrument 210 in that the housing 329 includes one or more alignment slots 333 similar to the alignment slots 233 described above. Further alignment may be provided in the housing 329 by an alignment groove 337 in communication with the alignment slot 333 of the housing 329. In one embodiment, the alignment groove 337 is contained in an extension 339 of the housing 329. It is envisioned that any number of the alignment grooves 337 can be used in the instrument 310, and furthermore that the location of the alignment grooves 337 may be varied depending on the particular design of the instrument 310. It is also envisioned that the shape of the alignment grooves 337 is not limited to the shape illustrated in FIGS. 18-20, but rather the shape can be any shape that assists in aligning the adjustment mechanism 322 with the housing 329.

Although not illustrated, it is envisioned that a biasing mechanism similar to the biasing mechanism 300 of the instrument 210 may be disposed between at least one of the first and second arms 324, 350 to bias at least one of the arms in either an open position or a closed position. Similarly, it is envisioned that a locking mechanism similar to the locking mechanisms 280 and 280' of the instrument 310 may be disposed between the first and second arms 324, 350 to maintain the handle portions 321, 351 in a desired position relative to one another. In one embodiment, a locking mechanism 380 may be coupled to either or both of the handle portions 321, 351 and may be effective to maintain the handle portions 321, 351 in a desired position relative to one another. The locking mechanism 380 may include a first bar 382 and a second bar 384 opposed to each other. Each of the first and second bars 382, 384 may also include teeth 383, which may be recessed in order to prevent undesired cutting of items such as surgical gloves. The teeth 383 of each of the opposed first and second bars 382, 384 may then engage each other such that the first and second bars 382, 384 are able to selectively engage each other to maintain the handle portions 321, 351 in a desired position relative to one another. One skilled in the art will appreciate that the locking mechanism described herein is just one of many different locking mechanisms that could be used to maintain the handle portions 321, 351 in a desired position relative to one another.

Figure 21:
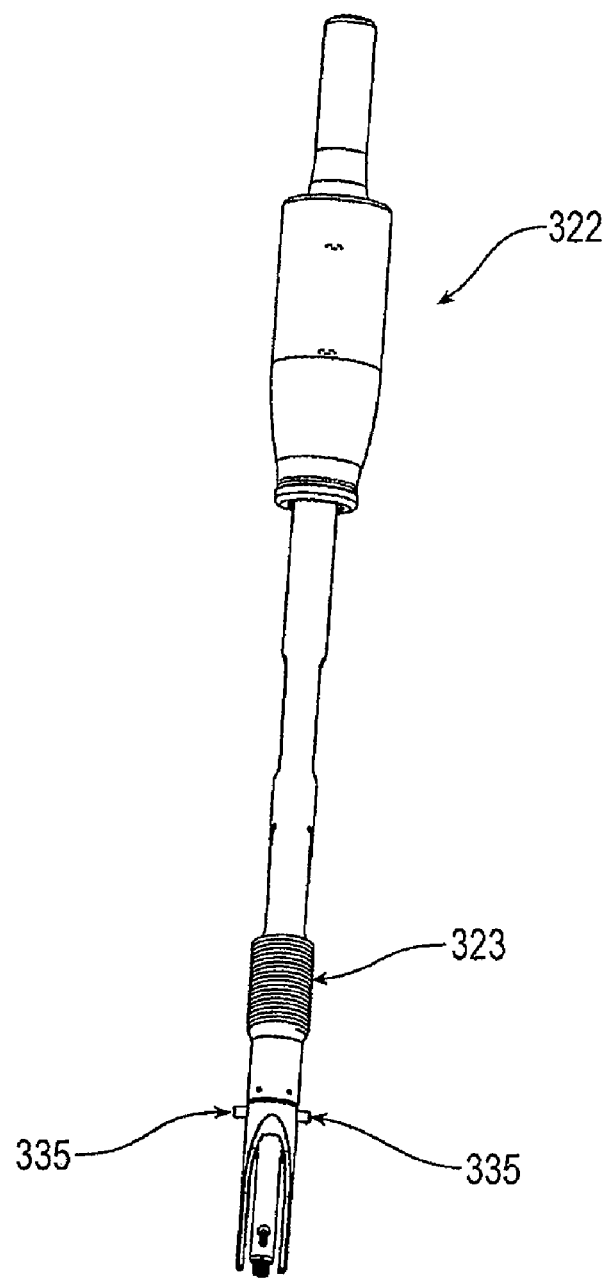
FIG. 21 is a front perspective view of the separate adjustment mechanism of the instrument of FIG. 18 which is configured to be removably and replaceably coupled to the housing of the instrument of FIG. 18.

Now referring to FIGS. 18 and 21, the adjustment mechanism 322 is of a similar design as the second adjustment mechanism 222 of the instrument 210. Thus, the adjustment mechanism 322 may include a threaded portion 323 in a location similar to the location of the threaded portion 223 of the second adjustment mechanism 222 of the instrument 210 and it may also interact with the threaded bore 331 of the housing 329 in a similar manner as described above with respect to the second adjustment mechanism 222. Additionally, the alignment feature(s) 335 are configured in a similar manner as described above for alignment feature(s) 235 of the second adjustment mechanism 222, and thus alignment feature(s) 335 operate in a similar manner. In the illustrated embodiment, the alignment features 335 are two opposed pins 335, although any other protruding structure capable of communicating with the alignment slot(s) 333 and the alignment groove(s) 337 may be used.

Like the second adjustment mechanism 222, the adjustment mechanism 322 may also be movable relative to the first and/or the second arm 324, 350 to adjust the spinal fixation element relative to the bone anchor in a second direction that is different to, e.g., at an angle to, the first direction. Because the adjustment mechanism 322 is so similar to the second adjustment mechanism 222, the adjustment mechanism operates in a similar, removable manner as described above, such that it may be used either independently or together with the first and second arms 324, 350.

In one embodiment of the instrument 310, the adjustment mechanism 322 may be configured to be operably aligned with the longitudinal axis M running through the center of the bone anchor. In another embodiment, the instrument 310 may include the handle portions 321, 351 respectively being oriented to be generally parallel to the adjustment mechanism 322 in a plane that is offset from the longitudinal axis M.

While the instruments and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. An instrument for manipulating a spinal fixation element relative to a bone anchor, the instrument comprising:
   a bone anchor grasping mechanism having a central axis and including a first arm having a proximal end with a handle portion located on a first side of the central axis, a distal end located on a second, opposite side of the central axis, the distal end having a guiding portion angled inwardly toward the central axis and being configured to engage a first receiving portion provided on the bone anchor, and an intermediate portion disposed between the proximal and distal ends, the intermediate portion having a housing through which the central axis extends from a proximal end of the mechanism to a distal end of the mechanism;
   a first adjustment mechanism including a second arm pivotally connected to the housing of the first arm, the second arm having a proximal end with a handle portion located on the second side of the central axis and a distal end located on the first side of the central axis, the distal end having a guiding portion angled inwardly toward the central axis and being configured to engage a second receiving portion provided on the bone anchor, the second arm being operable to adjust the spinal fixation element in a first direction upon pivoting relative to the first arm; and a second adjustment mechanism being movable relative to the bone anchor grasping mechanism to adjust the spinal fixation element in a second direction, generally perpendicular to the first direction, relative to the bone anchor.

2. The instrument of claim 1, wherein the housing includes a threaded bore and at least one alignment slot in communication with the threaded bore.

3. The instrument of claim 2, wherein the second adjustment mechanism includes a threaded portion configured to engage the threaded bore and at least one alignment feature distal of the threaded portion and configured to fit within the at least one alignment slot.

4. The instrument of claim 2, wherein an inner portion of the first arm includes at least one alignment groove in communication with the at least one alignment slot of the housing.

5. The instrument of claim 1, wherein the housing of the first arm includes a threaded bore formed therein and the second adjustment mechanism includes a threaded portion configured to be removably and replaceably coupled to the threaded bore of the housing.

6. The instrument of claim 1, further comprising a biasing mechanism configured to bias at least one of the handle portions of the first arm and the second arm to one of an open position and a closed position.

7. The instrument of claim 6, wherein the biasing mechanism is disposed between the handle portions of the first arm and the second arm.

8. The instrument of claim 6, wherein the biasing mechanism is a leaf spring.

9. The instrument of claim 8, wherein the leaf spring has a central opening formed therein that is configured to permit passage of the second adjustment mechanism therethrough.

10. The instrument of claim 6, further comprising a locking mechanism coupled to at least one of the handle portions of the first arm and the second arm, the locking mechanism being effective to maintain the handle portions of the first arm and the second arm in a desired position relative to one another.

11. The instrument of claim 10, wherein the locking mechanism comprises a rack pivotally mounted on one of the handle portions of the first arm and the second arm and extending towards the other of the first arm and the second arm, and a pawl formed on the other of the handle portions of the first arm and the second arm, the rack being able to pivot between a position in which it can be engaged by the pawl and a position in which it is not engageable by the pawl.

12. The instrument of claim 11, wherein when the rack is pivotably oriented at an angle other than zero relative to a plane of the handle portions of the first arm and the second arm.

13. The instrument of claim 1, wherein at least one of the handle portions of the first arm and the second arm is inherently flexible and is capable of storing potential energy as a result of a further closure force applied to the handle portions after the distal ends of the first arm and the second arm are engaged with the bone anchor.

14. The instrument of claim 13, wherein at least one of the handle portions of the first arm and the second arm is able to move a distance in the range of approximately 5 to 10 mm toward the other of the handle portions of the first arm and the second arm after the distal ends of the first arm and the second arm are engaged with the bone anchor.

15. An instrument for manipulating a spinal fixation element relative to a bone anchor, the instrument comprising:
a first arm having a proximal end with a handle portion and a distal end, the distal end having a guiding portion angled inwardly toward a central axis and being configured to engage a first receiving portion provided on the bone anchor;
a second arm pivotally connected to the first arm, the second arm having a proximal end with a handle portion and a distal end, the distal end having a guiding portion angled inwardly toward the central axis and being configured to engage a second receiving portion provided on the bone anchor, the first arm and the second arm being pivotable about a pivot axis that intersects the first arm and the second arm, the first arm and the second arm being operable to adjust the spinal fixation element in a first direction upon pivoting the first and second arms about the pivot axis, relative to each other;
a housing coupled to at least one of the first arm and the second arm; and
an adjustment mechanism being movable relative to at least one of the first arm and the second arm to adjust the spinal fixation element in a second direction, that is generally perpendicular to the first direction, relative to the bone anchor.

16. The instrument of claim 15, wherein the housing includes a threaded bore formed therein and the adjustment mechanism includes a threaded portion configured to selectively mate with the threaded bore of the housing.

17. The instrument of claim 15, wherein the adjustment mechanism is configured to be operably aligned with a longitudinal axis of the bone anchor.

18. The instrument of claim 17, wherein at least one of the handle portions of the first arm and the second arm is oriented to be generally parallel to the adjustment mechanism in a plane that is offset from the longitudinal axis of the bone anchor.

19. The instrument of claim 15, wherein the housing includes at least one alignment slot in communication with the threaded bore.

20. The instrument of claim 19, wherein a portion of the adjustment mechanism distal of the threaded portion includes at least one alignment feature configured to fit within the at least one alignment slot.

21. The instrument of claim 19, wherein the housing includes at least one alignment groove in communication with the at least one alignment slot of the housing.

22. The instrument of claim 15, further comprising a pivot at which the first and second arms are pivotally connected, the pivot being located at the pivot axis.

* * * * *